(12) United States Patent
Jager et al.

(10) Patent No.: US 7,795,379 B2
(45) Date of Patent: Sep. 14, 2010

(54) ISOLATED NUCLEIC ACID MOLECULES ENCODING CANCER ASSOCIATED ANTIGENS, THE ANTIGENS PER SE, AND USES THEREOF

(75) Inventors: Elke Jager, Frankfurt Am Main (DE); Dirk Jager, Frankfurt Am Main (DE); Alexander Knuth, Frankfurt Am Main (DE)

(73) Assignee: Ludwig Institute for Cancer Research, New York, NY (US)

( * ) Notice: Subject to any disclaimer, the term of this patent is extended or adjusted under 35 U.S.C. 154(b) by 339 days.

(21) Appl. No.: 11/220,785

(22) Filed: Sep. 6, 2005

(65) Prior Publication Data
US 2006/0165651 A1  Jul. 27, 2006

Related U.S. Application Data

(63) Continuation-in-part of application No. 10/729,340, filed on Dec. 4, 2003, now Pat. No. 7,354,992, and a continuation-in-part of application No. 09/602,362, filed on Jun. 22, 2000, now Pat. No. 6,911,529, which is a continuation-in-part of application No. 09/451,739, filed on Nov. 30, 1999, now Pat. No. 6,774,226.

(60) Provisional application No. 60/608,075, filed on Sep. 8, 2004, provisional application No. 60/430,869, filed on Dec. 4, 2002.

(51) Int. Cl.
*C07K 5/10* (2006.01)
(52) U.S. Cl. ...................................................... 530/300
(58) Field of Classification Search .................... None
See application file for complete search history.

(56) References Cited

U.S. PATENT DOCUMENTS 5,840,839 A * 11/1998 Wang et al. .................. 530/325
2002/0085998 A1* 7/2002 Jiang et al. ............... 424/93.21
2005/0112099 A1* 5/2005 Berinstein et al. .......... 424/93.2

FOREIGN PATENT DOCUMENTS

WO   WO2004/092212   * 10/2004

OTHER PUBLICATIONS

Roitt et al (Immunology, Fourth Edition, 1996, Mosby, p. 7.9-7.11.*
* cited by examiner

*Primary Examiner*—Misook Yu
*Assistant Examiner*—Mark Halvorson
(74) *Attorney, Agent, or Firm*—Fulbright & Jaworski LLP

(57) ABSTRACT

The invention relates to newly identified cancer associated antigens. It has been discovered that each of these molecules provokes antibodies when expressed by a subject. The ramifications of this observation are also a part of this invention.

23 Claims, 2 Drawing Sheets

SEQUENCE LISTING

<160> NUMBER OF SEQ ID NOS: 34

<210> SEQ ID NO 1
<211> LENGTH: 1533
<212> TYPE: DNA
<213> ORGANISM: Homo sapiens
<220> FEATURE:
<221> NAME/KEY: CDS
<222> LOCATION: 235
<223> OTHER INFORMATION: n is unknown

<400> SEQUENCE: 1

| | | | | | |
|---|---|---|---|---|---|
| ggttttccac | gttggacaag | tgcggctcgg | cggccagcgg | agcgcgcccc | ttcccgctgc | 60 |
| ccgctccgct | cctctcttct | acccagccca | gtgggcgagt | gggcagcggc | ggccgcggcg | 120 |
| ctgggccctc | tcccgccggt | gtgtgcgcgc | tcgtacgcgc | ggcccccggc | gccagccccg | 180 |
| ccgcctgaga | gggggcctgc | gccgccggcc | ggggcgtgcg | cccgggagcc | accgncaccg | 240 |
| cggcccgcgc | cctcaggcgc | tggggtcccc | gcggacccgg | aggcggcgga | cgggctcggc | 300 |
| agatgtagcc | gccgggccga | agcaggagcc | ggcggggggg | cgccgggaga | gcgagggctt | 360 |
| tgcattttgc | agtgctattt | tttgaggggg | gcggagggtg | gaggaagtcg | gaaagccgcg | 420 |
| ccgagtcgcc | ggggacctcc | ggggtgaacc | atgttgagtc | ctgccaacgg | ggagcagctc | 480 |
| cacctggtga | actatgtgga | ggactacctg | gactccatcg | agtccctgcc | tttcgacttg | 540 |
| cagagaaatg | tctcgctgat | gcgggagatc | gacgcgaaat | accaagagat | cctgaaggag | 600 |
| ctagacgagt | gctacgagcg | cttcagtcgc | gagacagacg | gggcgcagaa | gcggcggatg | 660 |
| ctgcactgtg | tgcagcgcgc | gctgatccgc | agccaggagc | tgggcgacga | gaagatccag | 720 |
| atcgtgagcc | agatggtgga | gctggtggag | aaccgcacgc | ggcaggtgga | cagccacgtg | 780 |
| gagctgttcg | aggcgcagca | ggagctgggc | gacacagcgg | gcaacagcgg | caaggctggc | 840 |
| gcggacaggc | ccaaaggcga | ggcggcagcg | caggctgaca | agcccaacag | caagcgctca | 900 |
| cggcggcagc | gcaacaacga | gaaccgtgag | aacgcgtcca | gcaaccacga | ccacgacgac | 960 |
| ggcgcctcgg | gcacacccaa | ggagaagaag | gccaagacct | ccaagaagaa | gaagcgctcc | 1020 |
| aaggccaagg | cggagcgaga | ggcgtcccct | gccgacctcc | ccatcgaccc | caacgaaccc | 1080 |
| acgtactgtc | tgtgcaacca | ggtctcctat | ggggagatga | tcggctgcga | caacgacgag | 1140 |
| tgccccatcg | agtggttcca | cttctcgtgc | gtggggctca | atcataaacc | caagggcaag | 1200 |
| tggtactgtc | ccaagtgccg | gggggagaac | gagaagacca | tggacaaagc | cctggagaaa | 1260 |
| tccaaaaaag | agagggctta | caacaggtag | tttgtggaca | ggcgcctggt | gtgaggagga | 1320 |
| caaaataaac | cgtgtattta | ttacattgct | gcctttgttg | aggtgcaagg | agtgtaaaat | 1380 |
| gtatattttt | aaagaatgtt | agaaaaggaa | ccattccttt | catagggatg | gcagtgattc | 1440 |
| tgtttgcctt | ttgttttcat | tggtacacgt | gtaacaagaa | agtggtctgt | ggatcagcat | 1500 |
| tttagaaact | acaaatatag | gtttgattca | aca | | | 1533 |

<210> SEQ ID NO 2
<211> LENGTH: 1143
<212> TYPE: DNA
<213> ORGANISM: Homo sapiens

<400> SEQUENCE: 2

| | | | | | |
|---|---|---|---|---|---|
| gagtaacccg | ataatatgcc | gttgtccggc | acggcgacga | gaattcccag | atatagcagt | 60 |
| agcagtgatc | ccgggcctgt | ggctcggggc | cggggctgca | gttcggaccg | cctcccgcga | 120 |

-continued

```
cccgcggggg ctcggagaca gtttcaggcc gcatctttgc tgacccgagg gtggggccgc      180
gcgtggccgt ggaaacagat cctgaaggag ctagacgagt gctacgagcg cttcagtcgc      240
gagacagacg gggcgcagaa gcggcggatg ctgcactgtg tgcagcgcgc gctgatccgc      300
agccaggagc tgggcgacga gaagatccag atcgtgagcc agatggtgga gctggtggag      360
aaccgcacgc ggcaggtgga cagccacgtg gagctgttcg aggcgcagca ggagctgggc      420
gacacagtgg gcaacagcgg caaggttggc gcggacaggc ccaatggcga tgcggtagcg      480
cagtctgaca agcccaacag caagcgctca cggcggcagc gcaacaacga gaaccgtgag      540
aacgcgtcca gcaaccacga ccacgacgac ggcgcctcgg gcacacccaa ggagaagaag      600
gccaagacct ccaagaagaa gaagcgctcc aaggccaagg cggagcgaga ggcgtcccct      660
gccgacctcc ccatcgaccc caacgaaccc acgtactgtc tgtgcaacca ggtctcctat      720
ggggagatga tcggctgcga caacgacgag tgccccatcg agtggttcca cttctcgtgc      780
gtggggctca atcataaacc caagggcaag tggtactgtc ccaagtgccg ggggagaac      840 gagaagacca tggacaaagc cctggagaaa tccaaaaaag agagggctta acacaggtag      900
tttgtggaca ggcgcctggt gtgaggagga caaaataaac cgtgtattta ttacattgct      960
gcctttgttg aggtgcaagg agtgtaaaat gtatattttt aaagaatgtt agaaaaggaa     1020
ccattccttt catagggatg gcagtgattc tgtttgcctt ttgttttcat tggtacacgt     1080
gtaacaagaa agtggtctgt ggatcagcat tttagaaact acaaatatag gtttgattca     1140
aca                                                                   1143
```

<210> SEQ ID NO 3
<211> LENGTH: 742
<212> TYPE: DNA
<213> ORGANISM: Homo sapiens

<400> SEQUENCE: 3

```
cgccgtccac accccagcgg ccctgacgct gtccctccg cgaccctcgc ctctggaaaa       60
agtgacaggc aaggccacgc ccccgcgagg gccggcctcg agcccgcagc ccccagggcc      120
tgggacgaga tcctgaagga gctagacgag tgctacgagc gcttcagtcg cgagacagac      180
ggggcgcaga agcggcggat gctgcactgt gtgcagcgcg cgctgatccg cagccaggag      240
ctgggcgacg agaagatcca gatcgtgagc cagatggtgg agctggtgga gaaccgcacg      300
cggcaggtgg acagccacgt ggagctgttc gaggcgcagc aggagctggg cgacacagcg      360
ggcaacagcg gcaaggctgg cgcggacagg cccaaggcg aggcggcagc gcaggctgac      420
aagcccaaca gcaagcgctc acggcggcag cgcaacaacg agaaccgtga gaacgcgtcc      480
agcaaccacg accacgacga cggcgcctcg ggcacaccca aggagaagaa ggccaagacc      540
tccaagaaga gaagcgctc caaggccaag gcggagcgag aggcgtcccc tgccgacctc      600
cccatcgacc ccaacgaacc cacgtactgt ctgtgcaacc aggtctccta tggggagatg      660
atcggctgcg acaacgacga gtgccccatc gagtggttcc acttctcgtg cgtgggctc      720 aatcataaac ccaagggcaa gt                                              742
```

<210> SEQ ID NO 4
<211> LENGTH: 857
<212> TYPE: DNA
<213> ORGANISM: Homo sapiens

<400> SEQUENCE: 4

-continued

```
cctccgagaa cggtgtccat ggcacagggc gggaagagat aaggcctagg gaaggcgccc    60
ctcgggccta tccacctctt ctggggctcg gcactaggaa gcagcttccc tctcaggccc   120
ctttgtctcc aagccgttcc aaactgagta ccgggagacg acacaaaggg agggcggtga   180
cggatggcgc aggcgcggga gccgcctagg ctgctgggag tggtggtccg gccgcggaat   240
ggagatcctg aaggagctag acgagtgcta cgagcgcttc agtcgcgaga cagacggggc   300
gcagaagcgg cggatgctgc actgtgtgca gcgcgcgctg atccgcagcc aggagctggg   360
cgacgagaag atccagatcg tgagccagat ggtggagctg gtggagaacc gcacgcggca   420
ggtggacagc cacgtggagc tgttcgaggc gcagcaggag ctgggcgaca cagcgggcaa   480
cagcggcaag gctggcgcgg acaggcccaa aggcgaggcg cagcgcagg ctgacaagcc    540 caacagcaag cgctcacggc ggcagcgcaa caacgagaac cgtgagaacg cgtccagcaa   600
ccacgaccac gacgacggcg cctcgggcac acccaaggag aagaaggcca agacctccaa   660
gaagaagaag cgctccaagg ccaaggcgga gcgagaggcg tcccctgccg acctccccat   720
cgaccccaac gaacccacgt actgtctgtg caaccaggtc tcctatgggg agatgatcgg   780
ctgcgacaac gacgagtgcc ccatcgagtg gttccacttc tcgtgcgtgg ggctcaatca   840
taaacccaag ggcaagt                                                  857
```

<210> SEQ ID NO 5
<211> LENGTH: 279
<212> TYPE: PRT
<213> ORGANISM: Homo sapiens

<400> SEQUENCE: 5

```
Met Leu Ser Pro Ala Asn Gly Glu Gln Leu His Leu Val Asn Tyr Val
1               5                   10                  15

Glu Asp Tyr Leu Asp Ser Ile Glu Ser Leu Pro Phe Asp Leu Gln Arg
            20                  25                  30

Asn Val Ser Leu Met Arg Glu Ile Asp Ala Lys Tyr Gln Glu Ile Leu
        35                  40                  45

Lys Glu Leu Asp Glu Cys Tyr Glu Arg Phe Ser Arg Glu Thr Asp Gly
50                  55                  60

Ala Gln Lys Arg Arg Met Leu His Cys Val Gln Arg Ala Leu Ile Arg
65                  70                  75                  80

Ser Gln Glu Leu Gly Asp Glu Lys Ile Gln Ile Val Ser Gln Met Val
                85                  90                  95

Glu Leu Val Glu Asn Arg Thr Arg Gln Val Asp Ser His Val Glu Leu
            100                 105                 110

Phe Glu Ala Gln Gln Glu Leu Gly Asp Thr Val Gly Asn Ser Gly Lys
        115                 120                 125

Val Gly Ala Asp Arg Pro Asn Gly Asp Ala Val Ala Gln Ser Asp Lys
130                 135                 140

Pro Asn Ser Lys Arg Ser Arg Arg Gln Arg Asn Asn Glu Asn Arg Glu
145                 150                 155                 160

Asn Ala Ser Ser Asn His Asp His Asp Asp Gly Ala Ser Gly Thr Pro
                165                 170                 175

Lys Glu Lys Lys Ala Lys Thr Ser Lys Lys Lys Arg Ser Lys Ala
            180                 185                 190

Lys Ala Glu Arg Glu Ala Ser Pro Ala Asp Leu Pro Ile Asp Pro Asn
        195                 200                 205

Glu Pro Thr Tyr Cys Leu Cys Asn Gln Val Ser Tyr Gly Glu Met Ile
210                 215                 220
```

-continued

```
Gly Cys Asp Asn Asp Glu Cys Pro Ile Glu Trp Phe His Phe Ser Cys
225                 230                 235                 240

Val Gly Leu Asn His Lys Pro Lys Gly Lys Trp Tyr Cys Pro Lys Cys
                245                 250                 255

Arg Gly Glu Asn Glu Lys Thr Met Asp Lys Ala Leu Glu Lys Ser Lys
                260                 265                 270

Lys Glu Arg Ala Tyr Asn Arg
        275
```

<210> SEQ ID NO 6
<211> LENGTH: 210
<212> TYPE: PRT
<213> ORGANISM: Homo sapiens

<400> SEQUENCE: 6

```
Met Leu His Cys Val Gln Arg Ala Leu Ile Arg Ser Gln Glu Leu Gly
1               5                   10                  15

Asp Glu Lys Ile Gln Ile Val Ser Gln Met Val Glu Leu Val Glu Asn
                20                  25                  30

Arg Thr Arg Gln Val Asp Ser His Val Glu Leu Phe Glu Ala Gln Gln
            35                  40                  45

Glu Leu Gly Asp Thr Val Gly Asn Ser Gly Lys Val Gly Ala Asp Arg
    50                  55                  60

Pro Asn Gly Asp Ala Val Ala Gln Ser Asp Lys Pro Asn Ser Lys Arg
65                  70                  75                  80

Ser Arg Arg Gln Arg Asn Asn Glu Asn Arg Glu Asn Ala Ser Ser Asn
                85                  90                  95

His Asp His Asp Asp Gly Ala Ser Gly Thr Pro Lys Glu Lys Lys Ala
                100                 105                 110

Lys Thr Ser Lys Lys Lys Lys Arg Ser Lys Ala Lys Ala Glu Arg Glu
            115                 120                 125

Ala Ser Pro Ala Asp Leu Pro Ile Asp Pro Asn Glu Pro Thr Tyr Cys
    130                 135                 140

Leu Cys Asn Gln Val Ser Tyr Gly Glu Met Ile Gly Cys Asp Asn Asp
145                 150                 155                 160

Glu Cys Pro Ile Glu Trp Phe His Phe Ser Cys Val Gly Leu Asn His
                165                 170                 175

Lys Pro Lys Gly Lys Trp Tyr Cys Pro Lys Cys Arg Gly Glu Asn Glu
                180                 185                 190

Lys Thr Met Asp Lys Ala Leu Glu Lys Ser Lys Lys Glu Arg Ala Tyr
            195                 200                 205

Asn Arg
    210
```

<210> SEQ ID NO 7
<211> LENGTH: 235
<212> TYPE: PRT
<213> ORGANISM: Homo sapiens

<400> SEQUENCE: 7

```
Met Glu Ile Leu Lys Glu Leu Asp Glu Cys Tyr Glu Arg Phe Ser Arg
1               5                   10                  15

Glu Thr Asp Gly Ala Gln Lys Arg Arg Met Leu His Cys Val Gln Arg
                20                  25                  30

Ala Leu Ile Arg Ser Gln Glu Leu Gly Asp Glu Lys Ile Gln Ile Val
            35                  40                  45
```

```
Ser Gln Met Val Glu Leu Val Glu Asn Arg Thr Arg Gln Val Asp Ser
 50                  55                  60
His Val Glu Leu Phe Glu Ala Gln Gln Glu Leu Gly Asp Thr Val Gly
 65                  70                  75                  80
Asn Ser Gly Lys Val Gly Ala Asp Arg Pro Asn Gly Asp Ala Val Ala
                 85                  90                  95
Gln Ser Asp Lys Pro Asn Ser Lys Arg Ser Arg Gly Arg Asn Asn
            100                 105                 110
Glu Asn Arg Glu Asn Ala Ser Ser His Asp His Asp Asp Gly Ala
            115                 120                 125
Ser Gly Thr Pro Lys Glu Lys Lys Ala Lys Thr Ser Lys Lys Lys
            130                 135                 140
Arg Ser Lys Ala Lys Ala Glu Arg Glu Ala Ser Pro Ala Asp Leu Pro
145                 150                 155                 160
Ile Asp Pro Asn Glu Pro Thr Tyr Cys Leu Cys Asn Gln Val Ser Tyr
                165                 170                 175
Gly Glu Met Ile Gly Cys Asp Asn Asp Glu Cys Pro Ile Glu Trp Phe
            180                 185                 190
His Phe Ser Cys Val Gly Leu Asn His Lys Pro Lys Gly Lys Trp Tyr
            195                 200                 205
Cys Pro Lys Cys Arg Gly Glu Asn Glu Lys Thr Met Asp Lys Ala Leu
    210                 215                 220
Glu Lys Ser Lys Lys Glu Arg Ala Tyr Asn Arg
225                 230                 235
```

<210> SEQ ID NO 8
<211> LENGTH: 772
<212> TYPE: DNA
<213> ORGANISM: Homo sapiens
<220> FEATURE:
<221> NAME/KEY: CDS
<222> LOCATION: 689,714
<223> OTHER INFORMATION: n is unknown

<400> SEQUENCE: 8

```
aaagcgttct cggcggcagc gcaacaacta gaaccgtgag aacgcgtcca gcaaccgcga      60
cccacgacga cgtcacctcg ggcacgccca aggagaagaa agcccagacc tctaagaaga     120
agcagggctc catggccaag gcgtagcggc aggcgtcccc cgcagacctc cccatcgacc     180
ccagcgagcc ctcctactgg gagatgatcc gctgcgacaa cgaatgcccc atcgagtggt     240
tccgcttctc gtgtgtgagt ctcaaccata aaccaaagcg caagtggtac tgttccagat     300
gccggggaaa gaacgatggg caaagccctt gagaagtcca gaaaaaaaac agggcttata     360
acaggtagtt tggggacatg cgtctaatag tgaggagaac aaaataagcc agtgtgttga     420
ttacattgcc acctttgctg aggtgcagga agtgtaaaat gtatattttt aaagaatgtt     480
gttagaggcc gggcgcggtg gctcacgcct gtaatcccag cactttggga ggccgaggcg     540
gtcggatcac gaggtcagga gatcgagacc atcctggcta acacggtgaa accccgtctc     600
tactaaaaat tcaaaaaaaa aattagctgg gcgtggtggc gggcgcctgt agtcccagct     660
attcgggagg ctgaggcagg agaatggcnt gaacctggga ggtggagctt gcantgagcc     720
aaggtcgcgc cactgcactc cagcctgggc gacagagcga gactccatct ta             772
```

<210> SEQ ID NO 9
<211> LENGTH: 32
<212> TYPE: DNA

<213> ORGANISM: Homo sapiens

<400> SEQUENCE: 9
cacacaggat ccatgttgag tcctgccaac gg                                    32

<210> SEQ ID NO 10
<211> LENGTH: 23
<212> TYPE: DNA
<213> ORGANISM: Homo sapiens

<400> SEQUENCE: 10
cgtggtcgtg gttgctggac gcg                                              23

<210> SEQ ID NO 11
<211> LENGTH: 21
<212> TYPE: DNA
<213> ORGANISM: Homo sapiens

<400> SEQUENCE: 11
cccagcggcc ctgacgctgt c                                                21

<210> SEQ ID NO 12
<211> LENGTH: 23
<212> TYPE: DNA
<213> ORGANISM: Homo sapiens

<400> SEQUENCE: 12
cgtggtcgtg gttgctggac gcg                                              23

<210> SEQ ID NO 13
<211> LENGTH: 23
<212> TYPE: DNA
<213> ORGANISM: Homo sapiens

<400> SEQUENCE: 13
ggaagagata aggcctaggg aag                                              23

<210> SEQ ID NO 14
<211> LENGTH: 23
<212> TYPE: DNA
<213> ORGANISM: Homo sapiens

<400> SEQUENCE: 14
cgtggtcgtg gttgctggac gcg                                              23

<210> SEQ ID NO 15
<211> LENGTH: 2030
<212> TYPE: DNA
<213> ORGANISM: Homo sapiens
<220> FEATURE:
<221> NAME/KEY: CDS
<222> LOCATION: 1628, 1752, 1758, 1769, 1789, 1873, 1908, 1915, 1933,
      1970, 1976, 2022
<223> OTHER INFORMATION: n is unknown

<400> SEQUENCE: 15
ctcgtgccgt taaagatggt cttctgaagg ctaactgcgg aatgaaagtt tctattccaa      60
ctaaagcctt agaattgatg gacatgcaaa ctttcaaagc agagcctccc gagaagccat     120
ctgccttcga gcctgccatt gaaatgcaaa agtctgttcc aaataaagcc ttggaattga     180
agaatgaaca acattgaga gcagatgaga tactcccatc agaatccaaa caaaaggact     240
atgaagaaag ttcttgggat tctgagagtc tctgtgagac tgtttcacag aaggatgtgt     300

-continued

```
gtttacccaa ggctacacat caaaaagaaa tagataaaat aaatggaaaa ttagaagagt    360
ctcctgataa tgatggtttt ctgaaggctc cctgcagaat gaaagtttct attccaacta    420
aagccttaga attgatggac atgcaaactt tcaaagcaga gcctcccgag aagccatctg    480
ccttcgagcc tgccattgaa atgcaaaagt ctgttccaaa taaagccttg gaattgaaga    540
atgaacaaac attgagagca gatcagatgt tcccttcaga atcaaaacaa agaaggttg     600
aagaaaattc ttgggattct gagagtctcc gtgagactgt tcacagaag gatgtgtgtg    660
tacccaaggc tacacatcaa aaagaaatgg ataaaataag tggaaaatta gaagattcaa    720
ctagccatc aaaaatcttg gatacagttc attcttgtga aagagcaagg aacttcaaa     780
aagatcactg tgaacaacgt acaggaaaaa tggaacaaat gaaaaagaag ttttgtgtac    840
tgaaaaagaa actgtcagaa gcaaagaaa taaaatcaca gttagagaac caaaagtta    900
aatgggaaca agagctctgc agtgtgagat tgactttaaa ccaagaagaa gagaagagaa    960
gaaatgccga tatattaaat gaaaaaatta gggaagaatt aggaagaatc gaagagcagc   1020
ataggaaaga gttagaagtg aaacaacaac ttgaacaggc tctcagaata caagatatag   1080
aattgaagag tgtagaaagt aatttgaatc aggtttctca cactcatgaa atgaaaaatt   1140
atctcttaca tgaaaattgc atgttgaaaa aggaaattgc catgctaaaa ctggaaatag   1200
ccacactgaa acaccaatac caggaaaagg aaaataaata ctttgaggac attaagattt   1260
taaaagaaaa gaatgctgaa cttcagatga ccctaaaact gaaagaggaa tcattaacta   1320
aaagggcatc tcaatatagt gggcagctta agttctgat agctgagaac acaatgctca    1380
cttctaaatt gaaggaaaaa caagacaaag aaatactaga ggcagaaatt gaatcacacc   1440
atcctagact ggcttctgct gtacaagacc atgatcaaat tgtgacatca agaaaaagtc   1500
aagaacctgc tttccacatt gcaggagatg cttgtttgca aagaaaaatg aatgttgatg   1560
tgagtagtac cgatatataa caatgaggtg ctccatcaac cactttctga agctcaaagg   1620
aaatccanaa gcctaaaaat taatctcaat tatgcaggag atgctctaag agaaaataca   1680
ttggtttcag gaacatgcac aaagagacca acgtgaaaca cagtgtcaaa tgaaggaagc   1740
tgaacacatg tntcaaancg aacaagatna tgtgaacaaa cacactganc agcaggagtc   1800
tctagatcag aaattatttc aactacaaag caaaaatatg tggcttcaac agcaattagt   1860
tcatgcacat aangaaagct gacaacaaaa gcaagataac aattgatntt cattntcttg   1920
agaggaaaat gcncatcatc ttctaaaaga gaaaaatgag gagatattn attacnataa   1980
ccatttaaaa aacccgtata tttcaatatg gaaaaaaaa anaaaaaaaa              2030
```

<210> SEQ ID NO 16
<211> LENGTH: 512
<212> TYPE: PRT
<213> ORGANISM: Homo sapiens

<400> SEQUENCE: 16

Met Lys Val Ser Ile Pro Thr Lys Ala Leu Glu Leu Met Asp Met Gln
1               5                   10                  15

Thr Phe Lys Ala Glu Pro Pro Glu Lys Pro Ser Ala Phe Glu Pro Ala
            20                  25                  30

Ile Glu Met Gln Lys Ser Val Pro Asn Lys Ala Leu Glu Leu Lys Asn
        35                  40                  45

Glu Gln Thr Leu Arg Ala Asp Glu Ile Leu Pro Ser Glu Ser Lys Gln
    50                  55                  60

Lys Asp Tyr Glu Glu Ser Ser Trp Asp Ser Glu Ser Leu Cys Glu Thr

```
                65                  70                  75                  80
Val Ser Gln Lys Asp Val Cys Leu Pro Lys Ala Thr His Gln Lys Glu
                    85                  90                  95
Ile Asp Lys Ile Asn Gly Lys Leu Glu Glu Ser Pro Asp Asn Asp Gly
                    100                 105                 110
Phe Leu Lys Ala Pro Cys Arg Met Lys Val Ser Ile Pro Thr Lys Ala
                    115                 120                 125
Leu Glu Leu Met Asp Met Gln Thr Phe Lys Ala Glu Pro Pro Glu Lys
                    130                 135                 140
Pro Ser Ala Phe Glu Pro Ala Ile Glu Met Gln Lys Ser Val Pro Asn
145                 150                 155                 160
Lys Ala Leu Glu Leu Lys Asn Glu Gln Thr Leu Arg Ala Asp Gln Met
                    165                 170                 175
Phe Pro Ser Glu Ser Lys Gln Lys Val Glu Glu Asn Ser Trp Asp
                    180                 185                 190
Ser Glu Ser Leu Arg Glu Thr Val Ser Gln Lys Asp Val Cys Val Pro
                    195                 200                 205
Lys Ala Thr His Gln Lys Glu Met Asp Lys Ile Ser Gly Lys Leu Glu
                    210                 215                 220
Asp Ser Thr Ser Leu Ser Lys Ile Leu Asp Thr Val His Ser Cys Glu
225                 230                 235                 240
Arg Ala Arg Glu Leu Gln Lys Asp His Cys Glu Gln Arg Thr Gly Lys
                    245                 250                 255
Met Glu Gln Met Lys Lys Phe Cys Val Leu Lys Lys Lys Leu Ser
                    260                 265                 270
Glu Ala Lys Glu Ile Lys Ser Gln Leu Glu Asn Gln Lys Val Lys Trp
                    275                 280                 285
Glu Gln Glu Leu Cys Ser Val Arg Leu Thr Leu Asn Gln Glu Glu Glu
                    290                 295                 300
Lys Arg Arg Asn Ala Asp Ile Leu Asn Glu Lys Ile Arg Glu Glu Leu
305                 310                 315                 320
Gly Arg Ile Glu Glu Gln His Arg Lys Glu Leu Glu Val Lys Gln Gln
                    325                 330                 335
Leu Glu Gln Ala Leu Arg Ile Gln Asp Ile Glu Leu Lys Ser Val Glu
                    340                 345                 350
Ser Asn Leu Asn Gln Val Ser His Thr His Glu Asn Glu Asn Tyr Leu
                    355                 360                 365
Leu His Glu Asn Cys Met Leu Lys Lys Glu Ile Ala Met Leu Lys Leu
                    370                 375                 380
Glu Ile Ala Thr Leu Lys His Gln Tyr Gln Glu Lys Glu Asn Lys Tyr
385                 390                 395                 400
Phe Glu Asp Ile Lys Ile Leu Lys Glu Lys Asn Ala Glu Leu Gln Met
                    405                 410                 415
Thr Leu Lys Leu Lys Glu Glu Ser Leu Thr Lys Arg Ala Ser Gln Tyr
                    420                 425                 430
Ser Gly Gln Leu Lys Val Leu Ile Ala Glu Asn Thr Met Leu Thr Ser
                    435                 440                 445
Lys Leu Lys Glu Lys Gln Asp Lys Glu Ile Leu Glu Ala Glu Ile Glu
                    450                 455                 460
Ser His His Pro Arg Leu Ala Ser Ala Val Gln Asp His Asp Gln Ile
465                 470                 475                 480
Val Thr Ser Arg Lys Ser Gln Glu Pro Ala Phe His Ile Ala Gly Asp
                    485                 490                 495
```

```
Ala Cys Leu Gln Arg Lys Met Asn Val Asp Val Ser Ser Thr Asp Ile
            500                 505                 510
```

<210> SEQ ID NO 17
<211> LENGTH: 33
<212> TYPE: DNA
<213> ORGANISM: Homo sapiens

<400> SEQUENCE: 17
cacacaggat ccatgcaggc cccgcacaag gag                                    33

<210> SEQ ID NO 18
<211> LENGTH: 34
<212> TYPE: DNA
<213> ORGANISM: Homo sapiens

<400> SEQUENCE: 18
cacacaaagc ttctaggatt tggcacagcc agag                                   34

<210> SEQ ID NO 19
<211> LENGTH: 294
<212> TYPE: PRT
<213> ORGANISM: Homo sapiens

<400> SEQUENCE: 19

```
Met Pro Leu Cys Thr Ala Thr Arg Ile Pro Arg Tyr Ser Ser Ser Ser
1               5                   10                  15

Asp Pro Gly Pro Val Ala Arg Gly Arg Gly Cys Ser Ser Asp Arg Leu
            20                  25                  30

Pro Arg Pro Ala Gly Pro Ala Arg Arg Gln Phe Gln Ala Ala Ser Leu
        35                  40                  45

Leu Thr Arg Gly Trp Gly Arg Ala Trp Pro Trp Lys Gln Ile Leu Lys
    50                  55                  60

Glu Leu Asp Glu Cys Tyr Glu Arg Phe Ser Arg Glu Thr Asp Gly Ala
65                  70                  75                  80

Gln Lys Arg Arg Met Leu His Cys Val Gln Arg Ala Leu Ile Arg Ser
                85                  90                  95

Gln Glu Leu Gly Asp Glu Lys Ile Gln Ile Val Ser Gln Met Val Glu
            100                 105                 110

Leu Val Glu Asn Arg Thr Arg Gln Val Asp Ser His Val Glu Leu Phe
        115                 120                 125

Glu Ala Gln Gln Glu Leu Gly Asp Thr Val Gly Asn Ser Gly Lys Val
    130                 135                 140

Gly Ala Asp Arg Pro Asn Gly Asp Ala Val Ala Gln Ser Asp Lys Pro
145                 150                 155                 160

Asn Ser Lys Arg Ser Arg Arg Gln Arg Asn Asn Glu Asn Arg Glu Asn
                165                 170                 175

Ala Ser Ser Asn His Asp His Asp Asp Gly Ala Ser Gly Thr Pro Lys
            180                 185                 190

Glu Lys Lys Ala Lys Thr Ser Lys Lys Lys Arg Ser Lys Ala Lys
        195                 200                 205

Ala Glu Arg Glu Ala Ser Pro Ala Asp Leu Pro Ile Asp Pro Asn Glu
    210                 215                 220

Pro Thr Tyr Cys Leu Cys Asn Gln Val Ser Tyr Gly Glu Met Ile Gly
225                 230                 235                 240

Cys Asp Asn Asp Glu Cys Pro Ile Glu Trp Phe His Phe Ser Cys Val
                245                 250                 255
```

-continued

Gly Leu Asn His Lys Pro Lys Gly Lys Trp Tyr Cys Pro Lys Cys Arg
          260                 265                 270

Gly Glu Asn Glu Lys Thr Met Asp Lys Ala Leu Glu Lys Ser Lys Lys
          275                 280                 285

Glu Arg Ala Tyr Asn Arg
        290

<210> SEQ ID NO 20
<211> LENGTH: 22
<212> TYPE: DNA
<213> ORGANISM: Homo sapiens

<400> SEQUENCE: 20
caaagcagag cctcccgaga ag                                              22

<210> SEQ ID NO 21
<211> LENGTH: 24
<212> TYPE: DNA
<213> ORGANISM: Homo sapiens

<400> SEQUENCE: 21
cctatgctgc tcttcgattc ttcc                                            24

<210> SEQ ID NO 22
<211> LENGTH: 4115
<212> TYPE: DNA
<213> ORGANISM: Homo sapiens

<400> SEQUENCE: 22
ctagtctata cagcaacgac cctacatcgt cactctgggg tcttagaaag tccataaagc      60
tgcctcccgg gacaagtccg aagctggaga gatgacaaag ggaagaagac atcaacctta     120
atatacaaga gcccagaaga gactgctcta actgggcctg gtcaatggcc tgaggaagta     180
gtaacatttc ggtagacaga agtgccagct gacgtccttg tggcgaacac ggacacctct     240
gatgaaggct acaatgccaa caggaggctt gcaaatatt tgatagattc ggtgccgata     300
taaatctcgt gatgtgtatg caacacggct tccattatgc gtttatagtg gattttgtca     360
gtggtggcaa actgctgtcc atggtgcagt atcgaagtgc caacaaggct gcctcacacc     420
acttttacta ccataacgaa agaagtgagc aattgtggaa ttttgctgat aaaaatgcaa     480
atgcgaatgc gttaataagt taaatgcaca ccctcatgct gctgtatgtc tggatcatca     540
gagatagttg catgcttctt agcaaaatgt gacgtctttg gcagatata gtggagtaac      600 tgcagaacat atgctgttac tgtggatttc tcacattcat aacaaattat gaatatatac     660
gaaaattatc aaaaatcatc aaataccaat cagaaggaac tctgcaggaa acctgatgag     720
gctgcaccct ggcggaaaga cacctgacac gctgaaagct ggtggaaaaa cacctgatga     780
ggctgcaccc tggtggaaag acacctgaca ggctgaaagc tggtggaaaa acacctgatg     840
aggctgcatc ttggtggagg aacatctgac aaattcaatg ttggagaaag gacatctgga     900
aagttcgaac gtcagcagaa aaacacctag gaaattacga tcctgcaaaa aaacatctga     960
gaaatttacg ggccagcaaa ggaagaccta agatcgcag ggagaaaaa gaagacacac      1020 ctagggaaat atgagtcccg aaaagaaaca ctgagaaatt acgtgggcag aaaaggaaga    1080
cctaggaaga cgcatgggag aaaagaaaac cctgtaaaga tggatgcgtg caagagtaac    1140
atctaataaa ctaaagtttt gaaaaaggaa atctaagatg ttgcatgtcc acaaaagaat    1200
catctacaaa gcaagtgcca tgatcagagg tcccatcaga tccaaacaag ggaagatgaa    1260

```
gaatattctt tgattctcgg gtctctttga agttctgcaa gattcaagtg gtatacctga   1320
gtctatatat aaaaagtaat gagataaata agaagtagaa agcctcctaa aagccatctg   1380
ccttcaagcc gccattgaaa gcaaaactct ttccaaataa gcctttgaat gaagaatgaa   1440
caaacattga agcagatccg tgttcccacc gaatccaaac aaaggactat aagaaaattc   1500
ttgggattct agagtctctg gagactgttt acagaaggat tgtgtttacc aaggctacac   1560
atcaaaaaga atagataaaa aaatggaaaa tagaagagtc cctaataaag tggtcttctg   1620
aaggctacct cggaatgaaa tttctattcc actaaagcct agaattgaag acatgcaaac   1680
tttcaaagcg agcctccggg aagccatctg cttcgagcct ccactgaaat caaaagtctg   1740
tcccaaataa gccttggaat gaaaatgaa aaacatggag gcagatgaga actcccatca    1800
gaatccaaac aaaggactat aagaaaattc tgggatactg gagtctctgt agactgtttc   1860
acagaaggat tgtgtttacc aaggctgcgc tcaaaaagaa tagataaaat aatggaaaat   1920
tagaagggtc cctgttaaag tggtcttctg aggctaactg ggaatgaaag ttctattcca   1980
actaaagcct agaattgatg acatgcaaac ttcaaagcag gcctcccgag agccatctgc   2040
cttcgagcct ccattgaaat caaaagtctg tccaaataaa ccttggaatt aagaatgaac   2100
aaacattgag gcagatgaga actcccatca aatccaaaca aaggactatg agaaagttct   2160
tgggattctg gagtctctgt agactgtttc cagaaggatg gtgtttaccc aggctacaca   2220
tcaaaaagaa tagataaaat aatggaaaat agagagtct ctgataatga ggttttctga    2280
aggctccctg agaatgaaag ttctattcca ctaaagcctt gaattgatgg catgcaaact   2340
ttcaaagcag gcctcccgag agccatctgc ttcgagcctg cattgaaatg aaaagtctgt   2400
tccaaataaa ccttggaatt aagaatgaac aacattgaga cagatcagat ttcccttcag   2460
aatcaaaaca agaaggttg agaaaattct gggattctga agtctccgtg gactgtttca    2520
cagaaggatg gtgtgtaccc aggctacaca caaaaagaaa ggataaaata gtggaaaatt   2580
agaagattca ctagcctatc aaaatcttgg tacagttcat cttgtgaaag gcaagggaac   2640
ttcaaaaaga cactgtgaac acgtacagga aaatggaaca atgaaaaaga gttttgtgta   2700
ctgaaaaaga actgtcagaa caaagaaat aaatcacagt agagaaccaa aagttaaatg     2760
ggaacaagag tctgcagtgt agattgactt aaaccaagaa aagagaagag agaaatgccg   2820
atatattaaa gaaaaaatta ggaagaatta gaagaatcga gagcagcata gaaagagtta   2880
gaagtgaaac acaacttgaa aggctctcag atacaagata agaattgaag gtgtagaaag   2940
taatttgaat aggttttctca actcatgaaa tgaaaattat tcttacatga aattgcatgt   3000
tgaaaaagga attgccatgc aaaactggaa tagccacact aaacaccaat ccaggaaaag   3060
gaaaataaat ctttgaggac ttaagatttt aaagaaaaga tgctgaactt agatgaccct   3120
aaaactgaaa aggaatcatt actaaaaggg atctcaatat gtgggcagct aaagttctga   3180
tagctgagaa acaatgctca ttctaaattg aggaaaaaca gacaaagaaa actagaggca   3240
gaaattgaat acaccatcct gactggcttc gctgtacaag ccatgatcaa ttgtgacatc   3300
aagaaaaagt aagaacctgc ttccacattg aggagatgct gtttgcaaag aaaatgaatg   3360
ttgatgtgag agtacgatat taacaatgag tgctccatca ccactttctg agctcaaagg   3420
aaatccaaaa cctaaaaatt atctcaatta gcaggagatg tctaagagaa atacattggt   3480
ttcagaacat cacaaagaga caacgtgaaa acagtgtcaa tgaaggaagc gaacacatgt   3540
atcaaaacga caagataatg aacaaacac ctgaacagca gagtctctag tcagaaatta     3600
```

-continued

```
tttcaactac aagcaaaaat tgtggcttca cagcaattag tcatgcacat agaaagctga    3660
caacaaaagc agataacaat gatattcatt tcttgagagg aaatgcaaca catctcctaa    3720
aagagaaaaa gaggagatat taattacaat accatttaaa aaccgtatat tcaatatgaa    3780
aaagagaaag agaaacagaa actcatgaga acaagcagta gaaacttctt tggagaaaca    3840
acagaccaga ctttactcac actcatgcta gaggccagtc tagcatcacc tatgttgaaa    3900
atcttaccaa agtctgtgtc acagaatact attttagaag aaaattcatg tttcttcctg    3960
aagcctacag cataaaataa agtgtgaaga ttacttgttc cgaattgcat aagctgcaca    4020
ggattcccat taccctgatg tgcagcagac tcattcaatc aaccagaatc cgctctgcac    4080
tccagcctag tgacagagtg gactccacct ggaaa                              4115
```

<210> SEQ ID NO 23
<211> LENGTH: 1341
<212> TYPE: PRT
<213> ORGANISM: Homo sapiens

<400> SEQUENCE: 23

```
Met Thr Lys Arg Lys Lys Thr Ile Asn Leu Asn Ile Gln Asp Ala Gln
1               5                   10                  15

Lys Arg Thr Ala Leu His Trp Ala Cys Val Asn Gly His Glu Glu Val
            20                  25                  30

Val Thr Phe Leu Val Asp Arg Lys Cys Gln Leu Asp Val Leu Asp Gly
        35                  40                  45

Glu His Arg Thr Pro Leu Met Lys Ala Leu Gln Cys His Gln Glu Ala
    50                  55                  60

Cys Ala Asn Ile Leu Ile Asp Ser Gly Ala Asp Ile Asn Leu Val Asp
65                  70                  75                  80

Val Tyr Gly Asn Met Ala Leu His Tyr Ala Val Tyr Ser Glu Ile Leu
                85                  90                  95

Ser Val Val Ala Lys Leu Leu Ser His Gly Ala Val Ile Glu Val His
            100                 105                 110

Asn Lys Ala Ser Leu Thr Pro Leu Leu Leu Ser Ile Thr Lys Arg Ser
        115                 120                 125

Glu Gln Ile Val Glu Phe Leu Leu Ile Lys Asn Ala Asn Ala Asn Ala
    130                 135                 140

Val Asn Lys Tyr Lys Cys Thr Ala Leu Met Leu Ala Val Cys His Gly
145                 150                 155                 160

Ser Ser Glu Ile Val Gly Met Leu Leu Gln Gln Asn Val Asp Val Phe
                165                 170                 175

Ala Ala Asp Ile Cys Gly Val Thr Ala Glu His Tyr Ala Val Thr Cys
            180                 185                 190

Gly Phe His His Ile His Glu Gln Ile Met Glu Tyr Ile Arg Lys Leu
        195                 200                 205

Ser Lys Asn His Gln Asn Thr Asn Pro Glu Gly Thr Ser Ala Gly Thr
    210                 215                 220

Pro Asp Glu Ala Ala Pro Leu Ala Glu Arg Thr Pro Asp Thr Ala Glu
225                 230                 235                 240

Ser Leu Val Glu Lys Thr Pro Asp Glu Ala Ala Pro Leu Val Glu Arg
                245                 250                 255

Thr Pro Asp Thr Ala Glu Ser Leu Val Glu Lys Thr Pro Asp Glu Ala
            260                 265                 270

Ala Ser Leu Val Glu Gly Thr Ser Asp Lys Ile Gln Cys Leu Glu Lys
        275                 280                 285
```

-continued

Ala Thr Ser Gly Lys Phe Glu Gln Ser Ala Glu Thr Pro Arg Glu
    290                 295                 300

Ile Thr Ser Pro Ala Lys Glu Thr Ser Glu Lys Phe Thr Trp Pro Ala
305                 310                 315                 320

Lys Gly Arg Pro Arg Lys Ile Ala Trp Glu Lys Lys Glu Asp Thr Pro
                325                 330                 335

Arg Glu Ile Met Ser Pro Ala Lys Glu Thr Ser Glu Lys Phe Thr Trp
            340                 345                 350

Ala Ala Lys Gly Arg Pro Arg Lys Ile Ala Trp Glu Lys Lys Glu Thr
        355                 360                 365

Pro Val Lys Thr Gly Cys Val Ala Arg Val Thr Ser Asn Lys Thr Lys
    370                 375                 380

Val Leu Glu Lys Gly Arg Ser Lys Met Ile Ala Cys Pro Thr Lys Glu
385                 390                 395                 400

Ser Ser Thr Lys Ala Ser Ala Asn Asp Gln Arg Phe Pro Ser Glu Ser
                405                 410                 415

Lys Gln Glu Glu Asp Glu Glu Tyr Ser Cys Asp Ser Arg Ser Leu Phe
            420                 425                 430

Glu Ser Ser Ala Lys Ile Gln Val Cys Ile Pro Glu Ser Ile Tyr Gln
        435                 440                 445

Lys Val Met Glu Ile Asn Arg Glu Val Glu Pro Pro Lys Lys Pro
    450                 455                 460

Ser Ala Phe Lys Pro Ala Ile Glu Met Gln Asn Ser Val Pro Asn Lys
465                 470                 475                 480

Ala Phe Glu Leu Lys Asn Glu Gln Thr Leu Arg Ala Asp Pro Met Phe
                485                 490                 495

Pro Pro Glu Ser Lys Gln Lys Asp Tyr Glu Glu Asn Ser Trp Asp Ser
            500                 505                 510

Glu Ser Leu Cys Glu Thr Val Ser Gln Lys Asp Val Cys Leu Pro Lys
        515                 520                 525

Ala Thr His Gln Lys Glu Ile Asp Lys Ile Asn Gly Lys Leu Glu Glu
    530                 535                 540

Ser Pro Asn Lys Asp Gly Leu Leu Lys Ala Thr Cys Gly Met Lys Val
545                 550                 555                 560

Ser Ile Pro Thr Lys Ala Leu Glu Leu Lys Asp Met Gln Thr Phe Lys
                565                 570                 575

Ala Glu Pro Pro Gly Lys Pro Ser Ala Phe Glu Pro Ala Thr Glu Met
            580                 585                 590

Gln Lys Ser Val Pro Asn Lys Ala Leu Glu Leu Lys Asn Glu Gln Thr
        595                 600                 605

Trp Arg Ala Asp Glu Ile Leu Pro Ser Glu Ser Lys Gln Lys Asp Tyr
    610                 615                 620

Glu Glu Asn Ser Trp Asp Thr Glu Ser Leu Cys Glu Thr Val Ser Gln
625                 630                 635                 640

Lys Asp Val Cys Leu Pro Lys Ala Ala His Gln Lys Glu Ile Asp Lys
                645                 650                 655

Ile Asn Gly Lys Leu Glu Gly Ser Pro Val Lys Asp Gly Leu Leu Lys
            660                 665                 670

Ala Asn Cys Gly Met Lys Val Ser Ile Pro Thr Lys Ala Leu Glu Leu
        675                 680                 685

Met Asp Met Gln Thr Phe Lys Ala Glu Pro Pro Glu Lys Pro Ser Ala
    690                 695                 700

```
Phe Glu Pro Ala Ile Glu Met Gln Lys Ser Val Pro Asn Lys Ala Leu
705                 710                 715                 720

Glu Leu Lys Asn Glu Gln Thr Leu Arg Ala Asp Glu Ile Leu Pro Ser
            725                 730                 735

Glu Ser Lys Gln Lys Asp Tyr Glu Glu Ser Ser Trp Asp Ser Glu Ser
            740                 745                 750

Leu Cys Glu Thr Val Ser Gln Lys Asp Val Cys Leu Pro Lys Ala Thr
        755                 760                 765

His Gln Lys Glu Ile Asp Lys Ile Asn Gly Lys Leu Glu Glu Ser Pro
    770                 775                 780

Asp Asn Asp Gly Phe Leu Lys Ala Pro Cys Arg Met Lys Val Ser Ile
785                 790                 795                 800

Pro Thr Lys Ala Leu Glu Leu Met Asp Met Gln Thr Phe Lys Ala Glu
                805                 810                 815

Pro Pro Glu Lys Pro Ser Ala Phe Glu Pro Ala Ile Glu Met Gln Lys
            820                 825                 830

Ser Val Pro Asn Lys Ala Leu Glu Leu Lys Asn Glu Gln Thr Leu Arg
            835                 840                 845

Ala Asp Gln Met Phe Pro Ser Glu Ser Lys Gln Lys Lys Val Glu Glu
    850                 855                 860

Asn Ser Trp Asp Ser Glu Ser Leu Arg Glu Thr Val Ser Gln Lys Asp
865                 870                 875                 880

Val Cys Val Pro Lys Ala Thr His Gln Lys Glu Met Asp Lys Ile Ser
            885                 890                 895

Gly Lys Leu Glu Asp Ser Thr Ser Leu Ser Lys Ile Leu Asp Thr Val
            900                 905                 910

His Ser Cys Glu Arg Ala Arg Glu Leu Gln Lys Asp His Cys Glu Gln
        915                 920                 925

Arg Thr Gly Lys Met Glu Gln Met Lys Lys Phe Cys Val Leu Lys
    930                 935                 940

Lys Leu Ser Glu Ala Lys Glu Ile Lys Ser Gln Leu Glu Asn Gln
945                 950                 955                 960

Lys Val Lys Trp Glu Gln Glu Leu Cys Ser Val Arg Leu Thr Leu Asn
                965                 970                 975

Gln Glu Glu Lys Arg Arg Asn Ala Asp Ile Leu Asn Glu Lys Ile
            980                 985                 990

Arg Glu Glu Leu Gly Arg Ile Glu  Glu Gln His Arg Lys  Glu Leu Glu
            995                 1000                1005

Val Lys  Gln Gln Leu Glu Gln  Ala Leu Arg Ile Gln  Asp Ile Glu Leu
    1010                1015                1020

Lys  Ser Val Glu Ser  Asn Leu Asn Gln Val Ser  His Thr His Glu Asn
1025                1030                1035                1040

Glu Asn Tyr Leu Leu  His Glu Asn Cys Met  Leu Lys Lys Glu Ile  Ala
            1045                1050                1055

Met Leu Lys Leu  Glu Ile Ala Thr Leu  Lys His Gln Tyr Gln  Glu Lys
                1060                1065                1070

Glu Asn Lys  Tyr Phe Glu Asp Ile  Lys Ile Leu Lys Glu  Lys Asn Ala
            1075                1080                1085

Glu Leu  Gln Met Thr Leu Lys  Leu Lys Glu Glu Ser  Leu Thr Lys Arg
        1090                1095                1100

Ala  Ser Gln Tyr Ser Gly  Gln Leu Lys Val Leu  Ile Ala Glu Asn Thr
1105                1110                1115                1120

Met Leu Thr Ser Lys  Leu Lys Glu Lys Gln  Asp Lys Glu Ile Leu  Glu
```

-continued

Ala Glu Ile Glu Ser His His Pro Arg Leu Ala Ser Ala Val Gln Asp
       1140                1145                1150

His Asp Gln Ile Val Thr Ser Arg Lys Ser Gln Glu Pro Ala Phe His
    1155                1160                1165

Ile Ala Gly Asp Ala Cys Leu Gln Arg Lys Met Asn Val Asp Val Ser
    1170                1175                1180

Ser Thr Ile Tyr Asn Asn Glu Val Leu His Gln Pro Leu Ser Glu Ala
1185                1190                1195                1200

Gln Arg Lys Ser Lys Ser Leu Lys Ile Asn Leu Asn Tyr Ala Gly Asp
            1205                1210                1215

Ala Leu Arg Glu Asn Thr Leu Val Ser Glu His Ala Gln Arg Asp Gln
            1220                1225                1230

Arg Glu Thr Gln Cys Gln Met Lys Glu Ala Glu His Met Tyr Gln Asn
            1235                1240                1245

Glu Gln Asp Asn Val Asn Lys His Thr Glu Gln Gln Glu Ser Leu Asp
    1250                1255                1260

Gln Lys Leu Phe Gln Leu Gln Ser Lys Asn Met Trp Leu Gln Gln Gln
1265            1270                1275                1280

Leu Val His Ala His Lys Lys Ala Asp Asn Lys Ser Lys Ile Thr Ile
                1285                1290                1295

Asp Ile His Phe Leu Glu Arg Lys Met Gln His His Leu Leu Lys Glu
            1300                1305                1310

Lys Asn Glu Glu Ile Phe Asn Tyr Asn Asn His Leu Lys Asn Arg Ile
    1315                1320                1325

Tyr Gln Tyr Glu Lys Glu Lys Ala Glu Thr Glu Asn Ser
1330                1335                1340

<210> SEQ ID NO 24
<211> LENGTH: 22
<212> TYPE: DNA
<213> ORGANISM: Homo sapiens

<400> SEQUENCE: 24
aatgggaaca agagctctgc ag                                              22

<210> SEQ ID NO 25
<211> LENGTH: 23
<212> TYPE: DNA
<213> ORGANISM: Homo sapiens

<400> SEQUENCE: 25
gggtcatctg aagttcagca ttc                                             23

<210> SEQ ID NO 26
<211> LENGTH: 3673
<212> TYPE: DNA
<213> ORGANISM: Homo sapiens
<220> FEATURE:
<221> NAME/KEY: CDS
<222> LOCATION: 439, 473, 1789
<223> OTHER INFORMATION: n is unknown

<400> SEQUENCE: 26
caagagcttg gcgatacaga aatttctgct ggtgttgggg cgggtgcggg aactgaagac     60
gggcgagtgc gagccggggg cgggtgctgg ggaagggtaa gcgggaagcg agggcgaggg    120
gtaggggctg gggaagggcg agcgggaggc gcgggctctc tctagcaggg ggctgcagcc    180

```
atgaagaggc tcttagctgc cgctggcaag ggcgtgcggg gcccgagcc cccgaacccc    240 ttcagcgaac gggtctacac tgagaaggac tacgggacca tctacttcgg ggatctaggg    300
aagatccata cagctgcctc ccggggccaa gtccagaagc tggagaagat gacagtaggg    360
aagaagcccg tcaacctgaa caaaagagat atgaagaaga ggactgctct acactgggcc    420
tgtgtcaatg ccatgcana agtagtaaca tttctggtag acagaaagtg ccngcttaat    480
gtccttgatg gcgaagggag gacacctctg atgaaggctc tacaatgcga gagggaagct    540
ttgtgcaaat attctcatag atgctggtgc tgatctaaat tatgtagatg tgtatggcaa    600
cacggctctc cattatgccg tttatagtga gaatttatta atggtggcaa cactgctgtc    660
ctatggtgca gtcatcgagg tgcaaaacaa ggctagcctc acaccccttt tactggccat    720
acagaaaaga agcaagcaaa ctgtggaatt tttactaaca aaaaatgcaa atgcaaacgc    780
atttaatgag tctaaatgca cagccctcat gcttgccata tgtgaaggct catcagagat    840
agtcggcatg cttcttcagc aaaatgttga cgtctttgct gaagacatac atggaataac    900
tgcagaacgt tatgctgctg ctcgtggagt taattacatt catcaacaac ttttggaaca    960
tatacgaaaa ttacctaaaa atcctcaaaa taccaatcca gaaggaacat ctacaggaac   1020
acctgatgag gctgcaccct tggcggaaag aacacctgac acggctgaaa gcttgctgga   1080
aaaaacacct gacgaggctg cacgcttggt ggagggaacg tctgccaaaa ttcaatgtct   1140
ggggaaagca acatctggaa agtttgaaca gtcaacagaa gaaacaccta ggaaaatttt   1200
gaggcctaca aaagaaacat ctgagaaatt ttcatggcca gcaaaagaaa gatctaggaa   1260
gatcacatgg gaggaaaaag aaacatctgt aaagactgaa tgcgtggcag gagtaacacc   1320
taataaaact gaagttttgg aaaaaggaac atctaatatg attgcatgtc ctacaaaaga   1380
aacatctaca aaagcaagta caaatgtgga tgtgagttct gtagagccta tattcagtct   1440
ttttggcaca cggactattg aaaattcaca gtgtacaaaa gttgaggaag actttaatct   1500
tgctaccaag attatctcta agagtgctgc acagaattat acgtgtttac ctgatgctac   1560
atatcaaaaa gatatcaaaa caataaatca caaaatagaa gatcagatgt tcccatcaga   1620
atccaaacga gaggaagatg aagaatattc ttgggattct gggagtctct tgagagttc   1680 tgcaaagact caagtgtgta tacctgagtc tatgtatcag aaagtaatgg agataaatag   1740
agaagtagaa gagcttcctg agaagccatc tgccttcaag cctgccgtng aaatgcaaaa   1800
gactgttcca aataaagcct ttgaattgaa gaatgaacaa acattgagag cagctcagat   1860
gttcccatca gaatccaaac aaaaggacga tgaagaaaat tcttgggatt ctgagagtcc   1920
ctgtgagacg gtttcacaga aggatgtgta tttacccaaa gctacacatc aaaaagaatt   1980 cgataccta agtggaaaat tagaagagtc tcctgttaaa gatggtcttc tgaagcctac   2040
ctgtggaagg aaagtttctc ttccaaataa agccttagaa ttaaaggaca gagaaacatt   2100
caaagcagag tctcctgata agatggtct tctgaagcct acctgtggaa ggaaagtttc   2160
tcttccaaat aaagccttag aattaaagga cagagaaaca ctcaaagcag agtctcctga   2220
taatgatggt cttctgaagc ctacctgtgg aaggaaagtt tctcttccaa ataaagcttt   2280
agaattgaag gacagagaaa cattcaaagc agctcagatg ttcccatcag aatccaaaca   2340
aaaggatgat gaagaaaatt cttgggattt tgagagtttc cttgagactc tcttacagaa   2400
tgatgtgtgt ttacccaagg ctacacatca aaaagaattc gatacctta gtggaaaatt   2460 agaagagtct cctgataaag atggtcttct gaagcctacc tgtggaatga aatttctct   2520 tccaaataaa gccttagaat tgaaggacag agaaacattc aaagcagagg atgtgagttc   2580
```

-continued

```
tgtagagtcc acattcagtc tttttggcaa accgactact gaaaattcac agtctacaaa    2640
agttgaggaa gactttaatc ttactaccaa ggagggagca acaaagacag taactggaca    2700
acaggaacgt gatattggca ttattgaacg agctccacaa gatcaaacaa ataagatgcc    2760
cacatcagaa ttaggaagaa aagaagatac aaaatcaact tcagattctg agattatctc    2820
tgtgagtgat acacagaatt atgagtgttt acctgaggct acatatcaaa agaaaataaa    2880
gacaacaaat ggcaaaatag aagagtctcc tgaaaagcct tctcactttg agcctgccac    2940
tgaaatgcaa aactctgttc caaataaagg cttagaatgg aagaataaac aaacattgag    3000
agcagattca actaccctat caaaaatctt ggatgcactt ccttcttgtg aaagaggaag    3060
ggaacttaaa aaagataact gtgaacaaat tacagcaaaa atggaacaaa tgaaaaataa    3120
gttttgtgta ctacaaaagg aactgtcaga agcgaaagaa ataaaatcac agttagagaa    3180
ccaaaaagct aaatgggaac aagagctctg cagtgtgaga ttgcctttaa atcaagaaga    3240
agagaagaga agaaatgtcg atatattaaa agaaaaaatt agacccgaag agcaacttag    3300 gaaaagtta gaagtgaaac accaacttga acagactctc agaatacaag atatagaatt    3360
gaaaagtgta acaagtaatt tgaatcaggt ttctcacact catgaaagtg aaaatgatct    3420
ctttcatgaa aattgcatgt tgaaaaagga aattgccatg ctaaaactgg aagtagccac    3480
actgaaacat caacaccagg tgaaggaaaa taaatacttt gaggacatta agattttaca    3540 agaaagaat gctgaacttc aaatgaccct aaaactgaaa cagaaaacag taacaaaaag    3600
ggcatctcag tatagagagc agcttaaagt tctgacggca gagaacacga tgctgacttc    3660
taaattgaag gaa                                                      3673
```

<210> SEQ ID NO 27
<211> LENGTH: 1011
<212> TYPE: PRT
<213> ORGANISM: Homo sapiens

<400> SEQUENCE: 27

Met Val Ala Thr Leu Leu Ser Tyr Gly Ala Val Ile Glu Val Gln Asn
1               5                   10                  15

Lys Ala Ser Leu Thr Pro Leu Leu Ala Ile Gln Lys Arg Ser Lys
            20                  25                  30

Gln Thr Val Glu Phe Leu Leu Thr Lys Asn Ala Asn Ala Asn Ala Phe
        35                  40                  45

Asn Glu Ser Lys Cys Thr Ala Leu Met Leu Ala Ile Cys Glu Gly Ser
    50                  55                  60

Ser Glu Ile Val Gly Met Leu Leu Gln Gln Asn Val Asp Val Phe Ala
65                  70                  75                  80

Glu Asp Ile His Gly Ile Thr Ala Glu Arg Tyr Ala Ala Arg Gly
                85                  90                  95

Val Asn Tyr Ile His Gln Gln Leu Leu Glu His Ile Arg Lys Leu Pro
            100                 105                 110

Lys Asn Pro Gln Asn Thr Asn Pro Glu Gly Thr Ser Thr Gly Thr Pro
        115                 120                 125

Asp Glu Ala Ala Pro Leu Ala Glu Arg Thr Pro Asp Thr Ala Glu Ser
    130                 135                 140

Leu Leu Glu Lys Thr Pro Asp Glu Ala Ala Arg Leu Val Glu Gly Thr
145                 150                 155                 160

Ser Ala Lys Ile Gln Cys Leu Gly Lys Ala Thr Ser Gly Lys Phe Glu
                165                 170                 175

```
Gln Ser Thr Glu Glu Thr Pro Arg Lys Ile Leu Arg Pro Thr Lys Glu
            180                 185                 190

Thr Ser Glu Lys Phe Ser Trp Pro Ala Lys Glu Arg Ser Arg Lys Ile
            195                 200                 205

Thr Trp Glu Glu Lys Glu Thr Ser Val Lys Thr Glu Cys Val Ala Gly
            210                 215                 220

Val Thr Pro Asn Lys Thr Glu Val Leu Glu Lys Gly Thr Ser Asn Met
225                 230                 235                 240

Ile Ala Cys Pro Thr Lys Glu Thr Ser Thr Lys Ala Ser Thr Asn Val
            245                 250                 255

Asp Val Ser Ser Val Glu Pro Ile Phe Ser Leu Phe Gly Thr Arg Thr
            260                 265                 270

Ile Glu Asn Ser Gln Cys Thr Lys Val Glu Glu Asp Phe Asn Leu Ala
            275                 280                 285

Thr Lys Ile Ile Ser Lys Ser Ala Ala Gln Asn Tyr Thr Cys Leu Pro
            290                 295                 300

Asp Ala Thr Tyr Gln Lys Asp Ile Lys Thr Ile Asn His Lys Ile Glu
305                 310                 315                 320

Asp Gln Met Phe Pro Ser Glu Ser Lys Arg Glu Asp Glu Glu Tyr
            325                 330                 335

Ser Trp Asp Ser Gly Ser Leu Phe Glu Ser Ser Ala Lys Thr Gln Val
            340                 345                 350

Cys Ile Pro Glu Ser Met Tyr Gln Lys Val Met Glu Ile Asn Arg Glu
            355                 360                 365

Val Glu Glu Leu Pro Glu Lys Pro Ser Ala Phe Lys Pro Ala Val Glu
            370                 375                 380

Met Gln Lys Thr Val Pro Asn Lys Ala Phe Glu Leu Lys Asn Glu Gln
385                 390                 395                 400

Thr Leu Arg Ala Ala Gln Met Phe Pro Ser Glu Ser Lys Gln Lys Asp
            405                 410                 415

Asp Glu Glu Asn Ser Trp Asp Ser Glu Ser Pro Cys Glu Thr Val Ser
            420                 425                 430

Gln Lys Asp Val Tyr Leu Pro Lys Ala Thr His Gln Lys Glu Phe Asp
            435                 440                 445

Thr Leu Ser Gly Lys Leu Glu Glu Ser Pro Val Lys Asp Gly Leu Leu
            450                 455                 460

Lys Pro Thr Cys Gly Arg Lys Val Ser Leu Pro Asn Lys Ala Leu Glu
465                 470                 475                 480

Leu Lys Asp Arg Glu Thr Phe Lys Ala Glu Ser Pro Asp Lys Asp Gly
            485                 490                 495

Leu Leu Lys Pro Thr Cys Gly Arg Lys Val Ser Leu Pro Asn Lys Ala
            500                 505                 510

Leu Glu Leu Lys Asp Arg Glu Thr Leu Lys Ala Glu Ser Pro Asp Asn
            515                 520                 525

Asp Gly Leu Leu Lys Pro Thr Cys Gly Arg Lys Val Ser Leu Pro Asn
530                 535                 540

Lys Ala Leu Glu Leu Lys Asp Arg Glu Thr Phe Lys Ala Ala Gln Met
545                 550                 555                 560

Phe Pro Ser Glu Ser Lys Gln Lys Asp Asp Glu Glu Asn Ser Trp Asp
            565                 570                 575

Phe Glu Ser Phe Leu Glu Thr Leu Leu Gln Asn Asp Val Cys Leu Pro
            580                 585                 590
```

```
Lys Ala Thr His Gln Lys Glu Phe Asp Thr Leu Ser Gly Lys Leu Glu
            595                 600                 605

Glu Ser Pro Asp Lys Asp Gly Leu Leu Lys Pro Thr Cys Gly Met Lys
            610                 615                 620

Ile Ser Leu Pro Asn Lys Ala Leu Glu Leu Lys Asp Arg Glu Thr Phe
625                 630                 635                 640

Lys Ala Glu Asp Val Ser Ser Val Glu Ser Thr Phe Ser Leu Phe Gly
            645                 650                 655

Lys Pro Thr Thr Glu Asn Ser Gln Ser Thr Lys Val Glu Glu Asp Phe
            660                 665                 670

Asn Leu Thr Thr Lys Glu Gly Ala Thr Lys Thr Val Thr Gly Gln Gln
            675                 680                 685

Glu Arg Asp Ile Gly Ile Ile Glu Arg Ala Pro Gln Asp Gln Thr Asn
            690                 695                 700

Lys Met Pro Thr Ser Glu Leu Gly Arg Lys Glu Asp Thr Lys Ser Thr
705                 710                 715                 720

Ser Asp Ser Glu Ile Ile Ser Val Ser Asp Thr Gln Asn Tyr Glu Cys
            725                 730                 735

Leu Pro Glu Ala Thr Tyr Gln Lys Glu Ile Lys Thr Thr Asn Gly Lys
            740                 745                 750

Ile Glu Glu Ser Pro Glu Lys Pro Ser His Phe Glu Pro Ala Thr Glu
            755                 760                 765

Met Gln Asn Ser Val Pro Asn Lys Gly Leu Glu Trp Lys Asn Lys Gln
            770                 775                 780

Thr Leu Arg Ala Asp Ser Thr Thr Leu Ser Lys Ile Leu Asp Ala Leu
785                 790                 795                 800

Pro Ser Cys Glu Arg Gly Arg Glu Leu Lys Lys Asp Asn Cys Glu Gln
            805                 810                 815

Ile Thr Ala Lys Met Glu Gln Met Lys Asn Lys Phe Cys Val Leu Gln
            820                 825                 830

Lys Glu Leu Ser Glu Ala Lys Glu Ile Lys Ser Gln Leu Glu Asn Gln
            835                 840                 845

Lys Ala Lys Trp Glu Gln Glu Leu Cys Ser Val Arg Leu Pro Leu Asn
            850                 855                 860

Gln Glu Glu Glu Lys Arg Arg Asn Val Asp Ile Leu Lys Glu Lys Ile
865                 870                 875                 880

Arg Pro Glu Glu Gln Leu Arg Lys Leu Glu Val Lys His Gln Leu
            885                 890                 895

Glu Gln Thr Leu Arg Ile Gln Asp Ile Glu Leu Lys Ser Val Thr Ser
            900                 905                 910

Asn Leu Asn Gln Val Ser His Thr His Glu Ser Glu Asn Asp Leu Phe
            915                 920                 925

His Glu Asn Cys Met Leu Lys Lys Glu Ile Ala Met Leu Lys Leu Glu
            930                 935                 940

Val Ala Thr Leu Lys His Gln His Gln Val Lys Glu Asn Lys Tyr Phe
945                 950                 955                 960

Glu Asp Ile Lys Ile Leu Gln Glu Lys Asn Ala Glu Leu Gln Met Thr
            965                 970                 975

Leu Lys Leu Lys Gln Lys Thr Val Thr Lys Arg Ala Ser Gln Tyr Arg
            980                 985                 990

Glu Gln Leu Lys Val Leu Thr Ala  Glu Asn Thr Met Leu  Thr Ser Lys
            995                  1000                 1005

Leu Lys  Glu
```

```
<210> SEQ ID NO 28
<211> LENGTH: 23
<212> TYPE: DNA
<213> ORGANISM: Homo sapiens

<400> SEQUENCE: 28
tctcatagat gctggtgctg atc                                              23

<210> SEQ ID NO 29
<211> LENGTH: 24
<212> TYPE: DNA
<213> ORGANISM: Homo sapiens

<400> SEQUENCE: 29
cccagacatt gaattttggc agac                                             24

<210> SEQ ID NO 30
<211> LENGTH: 56
<212> TYPE: PRT
<213> ORGANISM: Homo sapiens

<400> SEQUENCE: 30

Met Glu Glu Ile Ser Ala Ala Ala Val Lys Val Val Pro Gly Pro Glu
1               5                   10                  15

Arg Pro Ser Pro Phe Ser Gln Leu Val Tyr Thr Ser Asn Asp Ser Tyr
            20                  25                  30

Ile Val His Ser Gly Asp Leu Arg Lys Ile His Lys Ala Ala Ser Arg
        35                  40                  45

Gly Gln Val Arg Lys Leu Glu Lys
    50                  55

<210> SEQ ID NO 31
<211> LENGTH: 6297
<212> TYPE: DNA
<213> ORGANISM: Homo sapiens

<400> SEQUENCE: 31
atggaggaga tctctgccgc cgctgtcaag tcgtgccgg gcccggagcg cccgagccct        60
ttcagccagc tagtctatac cagcaacgac tcctacatcg tccactctgg ggatcttaga      120
aagatccata agctgcctc ccggggacaa gtccggaagc tggagaagat gacaaagagg       180
aagaagacca tcaaccttaa tatacaagac gcccagaaga ggactgctct acactgggcc      240
tgtgtcaatg gccatgagga agtagtaaca tttctggtag acagaaagtg ccagcttgac      300
gtccttgatg gcgaacacag gacacctctg atgaaggctc tacaatgcca tcaggaggct      360
tgtgcaaata ttctgataga ttctggtgcc gatataaatc tcgtagatgt gtatggcaac      420
acggctctcc attatgctgt ttatagtgag attttgtcag tggtggcaaa actgctgtcc      480
catggtgcag tcatcgaagt gcacaacaag ctagcctca caccacttt actatccata       540 acgaaaagaa gtgagcaaat tgtggaattt ttgctgataa aaaatgcaaa tcgaatgca       600 gttaataagt ataaatgcac agccctcatg cttgctgtat gtcatggatc atcagagata      660
gttggcatgc ttcttcagca aaatgttgac gtctttgctg cagatatatg tggagtaact      720
gcagaacatt atgctgttta ttgtggattt catcacattc atgaacaaat tatggaatat      780
atacgaaaat tatctaaaaa tcatcaaaat accaatccag aaggaacatc tgcaggaaca      840
cctgatgagg ctgcacccct tggcggaaaga acacctgaca cagctgaaag cttggtggaa     900
```

```
aaaacacctg atgaggctgc acccttggtg gaaagaacac ctgacacggc tgaaagcttg    960
gtggaaaaaa cacctgatga ggctgcatcc ttggtggagg aacatctga caaaattcaa   1020
tgtttggaga aagcgacatc tggaaagttc aacagtcag cagaagaaac acctagggaa   1080
attacgagtc ctgcaaaaga acatctgag aaatttacgt ggccagcaaa aggaagacct   1140
aggaagatcg catgggagaa aaagaagac acacctaggg aaattatgag tcccgcaaaa   1200
gaaacatctg agaaatttac gtgggcagca aaggaagac ctaggaagat cgcatgggag   1260
aaaaaagaaa cacctgtaaa gactggatgc gtggcaagaa taacatctaa taaaactaaa   1320
gttttggaaa aaggaagatc taagatgatt gcatgtccta caaagaatc atctacaaaa   1380
gcaagtgcca atgatcagag gttcccatca gaatccaaac aagaggaaga tgaagaatat   1440
tcttgtgatt ctcggagtct ctttgagagt tctgcaaaga ttcaagtgtg tatacctgag   1500
tctatatatc aaaagtaat ggagataaat agagaagtag aagagcctcc taagaagcca   1560
tctgccttca agcctgccat tgaaatgcaa aactctgttc caaataaagc ctttgaattg   1620
aagaatgaac aaacattgag agcagatccg atgttcccac cagaatccaa acaaaaggac   1680
tatgaagaaa attcttggga ttctgagagt ctctgtgaga ctgtttcaca gaaggatgtg   1740
tgtttaccca aggctacaca tcaaaaagaa atagataaaa taaatggaaa attagaagag   1800
tctcctaata aagatggtct tctgaaggct acctgcggaa tgaaagtttc tattccaact   1860
aaagccttag aattgaagga catgcaaact ttcaaagcag agcctccggg gaagccatct   1920
gccttcgagc ctgccactga aatgcaaaag tctgtcccaa ataaagcctt ggaattgaaa   1980
aatgaacaaa cattgagagc agatgagata ctcccatcag aatccaaaga aaaggactat   2040
gaagaaaatt cttgggatac tgagagtctc tgtgagactg tttcacagaa ggatgtgtgt   2100
ttacccaagg ctgcgcatca aaagaaata gataaaataa atggaaaatt agaagggtct   2160
cctgttaaag atggtcttct gaaggctaac tgcggaatga agtttctat tccaactaaa   2220
gccttagaat tgatggacat gcaaactttc aaagcagagc ctcccgagaa gccatctgcc   2280
ttcgagcctg ccattgaaat gcaaaagtct gttccaaata aagccttgga attgaagaat   2340
gaacaaacat tgagagcaga tgagatactc ccatcagaat ccaaacaaaa ggactatgaa   2400
gaaagttctt gggattctga gagtctctgt gagactgttt cacagaagga tgtgtgttta   2460
cccaaggcta cacatcaaaa agaaatagat aaaataaatg gaaaattaga agagtctcct   2520
gataatgatg ttttctgaa ggctccctgc agaatgaaag tttctattcc aactaaagcc   2580
ttagaattga tggacatgca aactttcaaa gcagagcctc ccgagaagcc atctgccttc   2640
gagcctgcca ttgaaatgca aaagtctgtt ccaaataaag ccttggaatt gaagaatgaa   2700
caaacattga gagcagatca gatgttccct tcagaatcaa acaaaagaa ggttgaagaa   2760
aattcttggg attctgagag tctccgtgag actgtttcac agaaggatgt gtgtgtaccc   2820
aaggctacac atcaaaaaga aatggataaa ataagtggaa aattagaaga ttcaactagc   2880
ctatcaaaaa tcttggatac agttcattct tgtgaaagag caaggaact tcaaaaagat   2940
cactgtgaac aacgtacagg aaaaatggaa caaatgaaaa agaagttttg tgtactgaaa   3000
aagaaactgt cagaagcaaa agaaataaaa tcacagttag agaaccaaaa agttaaatgg   3060
gaacaagagc tctgcagtgt gagattgact ttaaaccaag aagaagagaa gagaagaaat   3120
gccgatatat aaatgaaaaa attagggaa gaattaggaa gaatcgaaga gcagcatagg   3180
aaagagttag aagtgaaaca acaacttgaa caggctctca gaatacaaga tatagaattg   3240
```

-continued

```
aagagtgtag aaagtaattt gaatcaggtt tctcacactc atgaaaatga aaattatctc    3300
ttacatgaaa attgcatgtt gaaaaggaa attgccatgc taaaactgga aatagccaca     3360
ctgaaacacc aataccagga aaaggaaaat aaatactttg aggacattaa gattttaaaa    3420
gaaaagaatg ctgaacttca gatgacccta aaactgaaag aggaatcatt aactaaaagg    3480
gcatctcaat atagtgggca gcttaaagtt ctgatagctg agaacacaat gctcacttct    3540
aaattgaagg aaaaacaaga caaagaaata ctagaggcag aaattgaatc acaccatcct    3600
agactggctt ctgctgtaca agaccatgat caaattgtga catcaagaaa aagtcaagaa    3660
cctgctttcc acattgcagg agatgcttgt ttgcaaagaa aaatgaatgt tgatgtgagt    3720
agtacgatat ataacaatga ggtgctccat caaccacttt ctgaagctca aggaaatcc    3780 aaaagcctaa aaattaatct caattatgcc ggagatgctc taagagaaaa tacattggtt    3840
tcagaacatg cacaaagaga ccaacgtgaa acacagtgtc aaatgaagga agctgaacac    3900
atgtatcaaa acgaacaaga taatgtgaac aaacacactg aacagcagga gtctctagat    3960
cagaaattat ttcaactaca aagcaaaaat atgtggcttc aacagcaatt agttcatgca    4020
cataagaaag ctgacaacaa aagcaagata acaattgata ttcatttcct tgagaggaaa    4080
atgcaacatc atctcctaaa agagaaaaat gaggagatat ttaattacaa taaccattta    4140
aaaaaccgta tatatcaata tgaaaagag aaagcagaaa cagaaaactc atgagagaca    4200
agcagtaaga aacttctttt ggagaaacaa cagaccagat ctttactcac aactcatgct    4260
aggaggccag tcctagcatc accttatgtt gaaaatctta ccaatagtct gtgtcaacag    4320
aatacttatt ttagaagaaa aattcatgat ttcttcctga agcctacaga cataaaataa    4380
cagtgtgaag aattacttgt tcacgaattg cataaagctg cacaggattc ccatctaccc    4440
tgatgatgca gcagacatca ttcaatccaa ccagaatctc gctctgtcac tcaggctgga    4500
gtgcagtggc gcaatctcgg ctcactgcaa actctgcctc ccaggttcac gccattctcc    4560
tgccacagcc tcccgagtag ctgggactac aggcgcccgc caccaagcac agctaagttt    4620
tttatttata gtagagacgg ggtttcactg tgttagccag gatggtctcg atctcctgac    4680
ctcgtgatct gcctgcctcg gcctcccaaa gtgccgggat tacaggcgtg agccaccgcg    4740
ccgggcctga tttcagtttc ttccagccct tcctattgtt aacatggggg ttgtgttgaa    4800
gaatataaag ttacaaagtc aaggaagtag gaaacatttt tacaagtatt atgtagccat    4860
cttggtgggg ctgtggtgag gtaggctgca aatgattctc ctatttcttt ccctgagttc    4920
agaacatagg aattagattg atagacatca acatacccgc tttattgctg actcatgaca    4980
actaatggga agacatggct cagatgtgca gccacagtga gcttctgaac atttcttctc    5040
agactaagct cttacacaca gttgcagttg aaagaaagaa ttgcttgaca tggccacagg    5100
agcaggcagc ttcctgcaga catgacagtc aacgcaaact catgtcactg tgggcagaca    5160
catgtttgca aagagactca gagccaaaca agcacactca atgtgctttg cccaaattta    5220
cccattaggt aaatcttccc tcctcccaag aagaaagtgg agagagcatg agtcctcaca    5280
tggaaacttg aagtcaggga aatgaaggct caccaattat ttgtgcatgg gtttaagttt    5340
tccttgaaat taagttcagg tttgtctttg tgtgtaccaa ttaatgacaa gaggttagat    5400
agaagtatgc tagatggcaa agagaaatat gttttgtgtc ttcaattttg ctaaaaataa    5460
cccagaacat ggataattca tttattaatt gattttggta agccaagtcc tatttggaga    5520
aaattaatag ttttttctaaa aaagaatttt ctcaatatca cctggcttga taacatttt     5580 ctccttcgag ttccttttc tggagtttaa caaacttgtt ctttacaaat agattatatt     5640
```

```
gactacctct cactgatgtt atgatattag tttctattgc ttactttgta tttctaattt      5700
taggattcac aatttagctg gagaactatt ttttaacctg ttgcacctaa acatgattga      5760
gctagaagac agttttacca tatgcatgca ttttctctga gttatatttt aaaatctata      5820
catttctcct aaatatggag gaaatcactg gcatcaaatg ccagtctcag acggaagacc      5880
taaagcccat ttctggcctg gagctacttg gctttgtgac ctatggtgag cataagtgc      5940 tctgagtttg tgttgcctct tttgtaaaat gagggtttga cttaatcagt gattttcata      6000
gcttaaaatt tttttgaaga acagaacttt ttttaaaaac agttagatgc aaccatatta      6060
tataaaacag aacagataca agtagagcta acttgctaaa gaaggatgg aggctctgaa       6120 gctgtgactt cattatccct taatactgct atgtcctctg tagtacctta gatttctatg      6180
ggacatcgtt taaaaactat tgtttatgcg agagccttgc taatttccta aaaattgtgg      6240
atacattttt tctcccatgt ataatttttct caccttctat ttaaaaaaaa aaaaaaa       6297
```

<210> SEQ ID NO 32
<211> LENGTH: 1397
<212> TYPE: PRT
<213> ORGANISM: Homo sapiens

<400> SEQUENCE: 32

```
Met Glu Glu Ile Ser Ala Ala Val Lys Val Pro Gly Pro Glu
                 5                  10                  15

Arg Pro Ser Pro Phe Ser Gln Leu Val Tyr Thr Ser Asn Asp Ser Tyr
                20                  25                  30

Ile Val His Ser Gly Asp Leu Arg Lys Ile His Lys Ala Ala Ser Arg
            35                  40                  45

Gly Gln Val Arg Lys Leu Glu Lys Met Thr Lys Arg Lys Lys Thr Ile
        50                  55                  60

Asn Leu Asn Ile Gln Asp Ala Gln Lys Arg Thr Ala Leu His Trp Ala
    65                  70                  75                  80

Cys Val Asn Gly His Glu Glu Val Thr Phe Leu Val Asp Arg Lys
                85                  90                  95

Cys Gln Leu Asp Val Leu Asp Gly Glu His Arg Thr Pro Leu Met Lys
            100                 105                 110

Ala Leu Gln Cys His Gln Glu Ala Cys Ala Asn Ile Leu Ile Asp Ser
        115                 120                 125

Gly Ala Asp Ile Asn Leu Val Asp Val Tyr Gly Asn Thr Ala Leu His
    130                 135                 140

Tyr Ala Val Tyr Ser Glu Ile Leu Ser Val Val Ala Lys Leu Leu Ser
145                 150                 155                 160

His Gly Ala Val Ile Glu Val His Asn Lys Ala Ser Leu Thr Pro Leu
                165                 170                 175

Leu Leu Ser Ile Thr Lys Arg Ser Glu Gln Ile Val Glu Phe Leu Leu
            180                 185                 190

Ile Lys Asn Ala Asn Ala Asn Ala Val Asn Lys Tyr Lys Cys Thr Ala
        195                 200                 205

Leu Met Leu Ala Val Cys His Gly Ser Ser Glu Ile Val Gly Met Leu
    210                 215                 220

Leu Gln Gln Asn Val Asp Val Phe Ala Ala Asp Ile Cys Gly Val Thr
225                 230                 235                 240

Ala Glu His Tyr Ala Val Thr Cys Gly Phe His His Ile His Glu Gln
                245                 250                 255
```

-continued

```
Ile Met Glu Tyr Ile Arg Lys Leu Ser Lys Asn His Gln Asn Thr Asn
            260                 265                 270
Pro Glu Gly Thr Ser Ala Gly Thr Pro Asp Glu Ala Ala Pro Leu Ala
            275                 280                 285
Glu Arg Thr Pro Asp Thr Ala Glu Ser Leu Val Glu Lys Thr Pro Asp
290                 295                 300
Glu Ala Ala Pro Leu Val Glu Arg Thr Pro Asp Thr Ala Glu Ser Leu
305                 310                 315                 320
Val Glu Lys Thr Pro Asp Glu Ala Ala Ser Leu Val Glu Gly Thr Ser
                325                 330                 335
Asp Lys Ile Gln Cys Leu Glu Lys Ala Thr Ser Gly Lys Phe Glu Gln
            340                 345                 350
Ser Ala Glu Glu Thr Pro Arg Glu Ile Thr Ser Pro Ala Lys Glu Thr
            355                 360                 365
Ser Glu Lys Phe Thr Trp Pro Ala Lys Gly Arg Pro Arg Lys Ile Ala
            370                 375                 380
Trp Glu Lys Lys Glu Asp Thr Pro Arg Glu Ile Met Ser Pro Ala Lys
385                 390                 395                 400
Glu Thr Ser Glu Lys Phe Thr Trp Ala Ala Lys Gly Arg Pro Arg Lys
                405                 410                 415
Ile Ala Trp Glu Lys Lys Glu Thr Pro Val Lys Thr Gly Cys Val Ala
            420                 425                 430
Arg Val Thr Ser Asn Lys Thr Lys Val Leu Glu Lys Gly Arg Ser Lys
            435                 440                 445
Met Ile Ala Cys Pro Thr Lys Glu Ser Ser Thr Lys Ala Ser Ala Asn
            450                 455                 460
Asp Gln Arg Phe Pro Ser Glu Ser Lys Gln Glu Glu Asp Glu Glu Tyr
465                 470                 475                 480
Ser Cys Asp Ser Arg Ser Leu Phe Glu Ser Ser Ala Lys Ile Gln Val
                485                 490                 495
Cys Ile Pro Glu Ser Ile Tyr Gln Lys Val Met Glu Ile Asn Arg Glu
            500                 505                 510
Val Glu Glu Pro Pro Lys Lys Pro Ser Ala Phe Lys Pro Ala Ile Glu
            515                 520                 525
Met Gln Asn Ser Val Pro Asn Lys Ala Phe Glu Leu Lys Asn Glu Gln
            530                 535                 540
Thr Leu Arg Ala Asp Pro Met Phe Pro Pro Glu Ser Lys Gln Lys Asp
545                 550                 555                 560
Tyr Glu Glu Asn Ser Trp Asp Ser Glu Ser Leu Cys Glu Thr Val Ser
                565                 570                 575
Gln Lys Asp Val Cys Leu Pro Lys Ala Thr His Gln Lys Glu Ile Asp
            580                 585                 590
Lys Ile Asn Gly Lys Leu Glu Glu Ser Pro Asn Lys Asp Gly Leu Leu
            595                 600                 605
Lys Ala Thr Cys Gly Met Lys Val Ser Ile Pro Thr Lys Ala Leu Glu
            610                 615                 620
Leu Lys Asp Met Gln Thr Phe Lys Ala Glu Pro Gly Lys Pro Lys Ser
625                 630                 635                 640
Ala Phe Glu Pro Ala Thr Glu Met Gln Lys Ser Val Pro Asn Lys Ala
                645                 650                 655
Leu Glu Leu Lys Asn Glu Gln Thr Leu Arg Ala Asp Glu Ile Leu Pro
            660                 665                 670
Ser Glu Ser Lys Glu Lys Asp Tyr Glu Glu Asn Ser Trp Asp Thr Glu
```

-continued

```
                675                 680                 685
Ser Leu Cys Glu Thr Val Ser Gln Lys Asp Val Cys Leu Pro Lys Ala
690                 695                 700

Ala His Gln Lys Glu Ile Asp Lys Ile Asn Gly Lys Leu Glu Gly Ser
705                 710                 715                 720

Pro Val Lys Asp Gly Leu Leu Lys Ala Asn Cys Gly Met Lys Val Ser
                725                 730                 735

Ile Pro Thr Lys Ala Leu Glu Leu Met Asp Met Gln Thr Phe Lys Ala
                740                 745                 750

Glu Pro Pro Glu Lys Pro Ser Ala Phe Glu Pro Ala Ile Glu Met Gln
                755                 760                 765

Lys Ser Val Pro Asn Lys Ala Leu Glu Leu Lys Asn Glu Gln Thr Leu
770                 775                 780

Arg Ala Asp Glu Ile Leu Pro Ser Glu Ser Lys Gln Lys Asp Tyr Glu
785                 790                 795                 800

Glu Ser Ser Trp Asp Ser Glu Ser Leu Cys Glu Thr Val Ser Gln Lys
                805                 810                 815

Asp Val Cys Leu Pro Lys Ala Thr His Gln Lys Glu Ile Asp Lys Ile
                820                 825                 830

Asn Gly Lys Leu Glu Glu Ser Pro Asp Asn Asp Gly Phe Leu Lys Ala
                835                 840                 845

Pro Cys Arg Met Lys Val Ser Ile Pro Thr Lys Ala Leu Glu Leu Met
                850                 855                 860

Asp Met Gln Thr Phe Lys Ala Glu Pro Pro Glu Lys Pro Ser Ala Phe
865                 870                 875                 880

Glu Pro Ala Ile Glu Met Gln Lys Ser Val Pro Asn Lys Ala Leu Glu
                885                 890                 895

Leu Lys Asn Glu Gln Thr Leu Arg Ala Asp Gln Met Phe Pro Ser Glu
                900                 905                 910

Ser Lys Gln Lys Lys Val Glu Asn Ser Trp Asp Ser Glu Ser Leu
                915                 920                 925

Arg Glu Thr Val Ser Gln Lys Asp Val Cys Val Pro Lys Ala Thr His
930                 935                 940

Gln Lys Glu Met Asp Lys Ile Ser Gly Lys Leu Glu Asp Ser Thr Ser
945                 950                 955                 960

Leu Ser Lys Ile Leu Asp Thr Val His Ser Cys Glu Arg Ala Arg Glu
                965                 970                 975

Leu Gln Lys Asp His Cys Glu Gln Arg Thr Gly Lys Met Glu Gln Met
                980                 985                 990

Lys Lys Lys Phe Cys Val Leu Lys Lys Lys Leu Ser Glu Ala Lys Glu
                995                 1000                1005

Ile Lys Ser Gln Leu Glu Asn Gln Lys Val Lys Trp Glu Gln Glu Leu
                1010                1015                1020

Cys Ser Val Arg Leu Thr Leu Asn Gln Glu Glu Lys Arg Arg Asn
1025                1030                1035                1040

Ala Asp Ile Leu Asn Glu Lys Ile Arg Glu Glu Leu Gly Arg Ile Glu
                1045                1050                1055

Glu Gln His Arg Lys Glu Leu Glu Val Lys Gln Gln Leu Glu Gln Ala
                1060                1065                1070

Leu Arg Ile Gln Asp Ile Glu Leu Lys Ser Val Glu Ser Asn Leu Asn
                1075                1080                1085

Gln Val Ser His Thr His Glu Asn Glu Asn Tyr Leu Leu His Glu Asn
                1090                1095                1100
```

-continued

```
Cys Met Leu Lys Lys Glu Ile Ala Met Leu Lys Leu Glu Ile Ala Thr
1105                1110                1115                1120

Leu Lys His Gln Tyr Gln Glu Lys Glu Asn Lys Tyr Phe Glu Asp Ile
            1125                1130                1135

Lys Ile Leu Lys Glu Lys Asn Ala Glu Leu Gln Met Thr Leu Lys Leu
        1140                1145                1150

Lys Glu Glu Ser Leu Thr Lys Arg Ala Ser Gln Tyr Ser Gly Gln Leu
        1155                1160                1165

Lys Val Leu Ile Ala Glu Asn Thr Met Leu Thr Ser Lys Leu Lys Glu
        1170                1175                1180

Lys Gln Asp Lys Glu Ile Leu Glu Ala Glu Ile Glu Ser His His Pro
1185                1190                1195                1200

Arg Leu Ala Ser Ala Val Gln Asp His Asp Gln Ile Val Thr Ser Arg
                1205                1210                1215

Lys Ser Gln Glu Pro Ala Phe His Ile Ala Gly Asp Ala Cys Leu Gln
            1220                1225                1230

Arg Lys Met Asn Val Asp Val Ser Ser Thr Ile Tyr Asn Asn Glu Val
            1235                1240                1245

Leu His Gln Pro Leu Ser Glu Ala Gln Arg Lys Ser Lys Ser Leu Lys
    1250                1255                1260

Ile Asn Leu Asn Tyr Ala Gly Asp Ala Leu Arg Glu Asn Thr Leu Val
1265                1270                1275                1280

Ser Glu His Ala Gln Arg Asp Gln Arg Glu Thr Gln Cys Gln Met Lys
            1285                1290                1295

Glu Ala Glu His Met Tyr Gln Asn Glu Gln Asp Asn Val Asn Lys His
            1300                1305                1310

Thr Glu Gln Gln Glu Ser Leu Asp Gln Lys Leu Phe Gln Leu Gln Ser
        1315                1320                1325

Lys Asn Met Trp Leu Gln Gln Leu Val His Ala His Lys Lys Ala
    1330                1335                1340

Asp Asn Lys Ser Lys Ile Thr Ile Asp Ile His Phe Leu Glu Arg Lys
1345                1350                1355                1360

Met Gln His His Leu Leu Lys Glu Lys Asn Glu Glu Ile Phe Asn Tyr
            1365                1370                1375

Asn Asn His Leu Lys Asn Arg Ile Tyr Gln Tyr Glu Lys Glu Lys Ala
            1380                1385                1390

Glu Thr Glu Asn Ser
        1395

<210> SEQ ID NO 33
<211> LENGTH: 22
<212> TYPE: DNA
<213> ORGANISM: Homo sapiens

<400> SEQUENCE: 33
caaagcagag cctcccgaga ag                                            22

<210> SEQ ID NO 34
<211> LENGTH: 24
<212> TYPE: DNA
<213> ORGANISM: Homo sapiens

<400> SEQUENCE: 34
cctatgctgc tcttcgattc ttcc                                          24
```

US 7,795,379 B2

ISOLATED NUCLEIC ACID MOLECULES ENCODING CANCER ASSOCIATED ANTIGENS, THE ANTIGENS PER SE, AND USES THEREOF

RELATED APPLICATION

This application claims priority from U.S. provisional application No. 60/608,075 filed Sep. 8, 2004, incorporated by reference in its entirety.

This application is a continuation in part of application Ser. No. 10/729,340, filed Dec. 4, 2003, now U.S. Pat. No. 7,354,992 which claims priority of Ser. No. 60/430,869, filed Dec. 4, 2002, and is also a continuation in part of Ser. No. 09/602,362, filed Jun. 22, 2000, now U.S. Pat. No. 6,911,529, which is a continuation in part of Ser. No. 09/451,739, filed Nov. 30, 1999, now U.S. Pat. No. 6,774,226.

FIELD OF THE INVENTION

This invention relates to antigens associated with cancer, the nucleic acid molecules encoding them, as well as the uses of these.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

Two basic strategies have been employed for the detection of such antigens, in e.g., human tumors. These will be referred to as the genetic approach and the biochemical approach. The genetic approach is exemplified by, e.g., dePlaen, et al., *Proc. Natl. Sci. USA*, 85:2275 (1988), incorporated by reference. In this approach, several hundred pools of plasmids of a cDNA library obtained from a tumor are transfected into recipient cells, such as COS cells, or into antigen-negative variants of tumor cell lines which are tested for the expression of the specific antigen. The biochemical approach, exemplified by, e.g., O. Mandelboim, et al., *Nature*, 369:69 (1994) incorporated by reference, is based on acidic elution of peptides which have bound to MHC-class I molecules of tumor cells, followed by reversed-phase high performance liquid chromatography (HPLC). Antigenic peptides are identified after they bind to empty MHC-class I molecules of mutant cell lines, defective in antigen processing, and induce specific reactions with cytotoxic T-lymphocytes. These reactions include induction of CTL proliferation, TNF release, and lysis of target cells, measurable in an MTT assay, or a 51Cr release assay.

These two approaches to the molecular definition of antigens have the following disadvantages: first, they are enormously cumbersome, time-consuming and expensive; and second, they depend on the establishment of cytotoxic T cell lines (CTLs) with predefined specificity.

The problems inherent to the two known approaches for the identification and molecular definition of antigens is best demonstrated by the fact that both methods have, so far, succeeded in defining only very few new antigens in human tumors. See, e.g., van der Bruggen, et al., *Science*, 254:1643-1647 (1991); Brichard, et al., *J. Exp. Med.*, 178:489-495 (1993); Coulie, et al., *J. Exp. Med.*, 180:35-42 (1994); Kawakami, et al., *Proc. Natl. Acad. Sci. USA*, 91:3515-3519 (1994).

Further, the methodologies described rely on the availability of established, permanent cell lines of the cancer type under consideration. It is very difficult to establish cell lines from certain cancer types, as is shown by, e.g., Oettgen, et al., *Immunol. Allerg. Clin. North. Am.*, 10:607-637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., *Proc. Natl. Acad. Sci. USA*, 92:11810-11913 (1995), incorporated by reference. Also, see U.S. Pat. No. 5,698,396. These references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent and Sahin, et al., supra, as well as Crew, et al., *EMBO J.*, 144:2333-2340 (1995), also incorporated by reference.

This methodology has been applied to a range of tumor types, including those described by Sahin, et al., supra, and Pfreundschuh, supra, as well as to esophageal cancer (Chen, et al., *Proc. Natl. Acad. Sci. USA*, 94:1914-1918 (1997)); lung cancer (Güre, et al., *Cancer Res.*, 58:1034-1041 (1998)); colon cancer (Ser. No. 08/948,705 filed Oct. 10, 1997) incorporated by reference, and so forth. Among the antigens identified via SEREX are the SSX2 molecule (Sahin, et al., *Proc. Natl. Acad. Sci. USA*, 92:11810-11813 (1995); Tureci, et al., *Cancer Res.*, 56:4766-4772 (1996); NY-ESO-1 Chen, et al., *Proc. Natl. Acad. Sci. USA*, 94:1914-1918 (1997); and SCP1 (U.S. Pat. No. 6,043,084) incorporated by reference. Analysis of SEREX identified antigens has shown overlap between SEREX defined and CTL defined antigens. MAGE-1, tyrosinase, and NY-ESO-1 have all been shown to be recognized by patient antibodies as well as CTLs, showing that humoral and cell mediated responses do act in concert.

It is clear from this summary that identification of relevant antigens via SEREX is a desirable aim. The inventors have applied this methodology and have identified several new antigens associated with cancer, as detailed in the description which follows.

DETAILED DESCRIPTION OF PREFERRED EMBODIMENTS

Example 1

Figure 1:
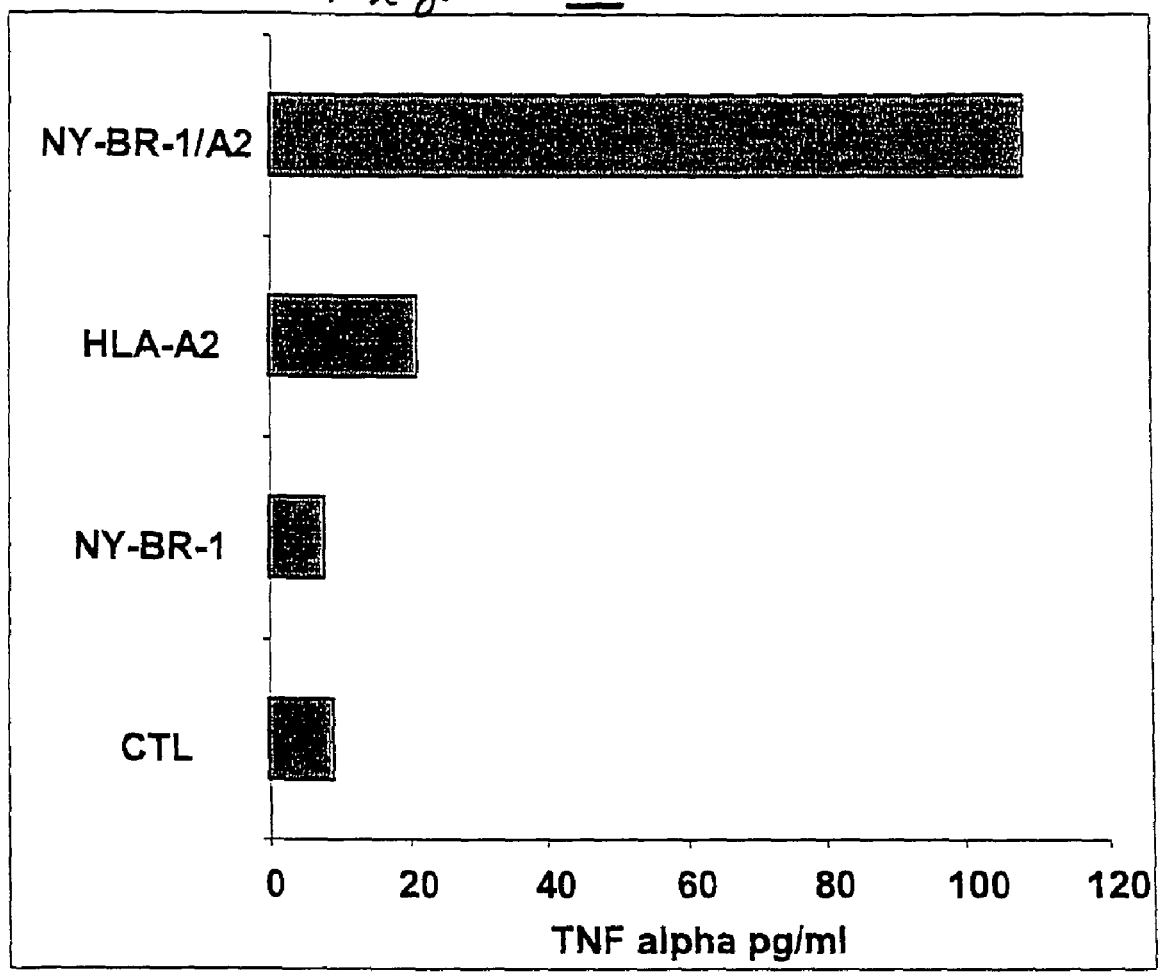
FIGS. 1-3, inclusive, show that NY-BR-1 is processed to peptides that are recognized by naturally occurring, CD8$^+$ cells.

The SEREX methodology, as described by, e.g. Sahin, et al., *Proc. Natl. Acad. Sci. USA*, 92:11810-11813 (1995); Chen, et al., *Proc. Natl. Acad. Sci. USA*, 94:1914-1918 (1997), and U.S. Pat. No. 5,698,396, all of which are incorporated by reference. In brief, total RNA was extracted from a sample of a cutaneous metastasis of a breast cancer patient (referred to as "BR11" hereafter), using standard CsCl guanidine thiocyanate gradient methodologies. A cDNA library was then prepared, using commercially available kits designed for this purpose. Following the SEREX methodology referred to supra, this cDNA expression library was amplified, and screened with either autologous BR11 serum which had been diluted to 1:200, or with allogeneic, pooled serum, obtained from 7 different breast cancer patients, which had been diluted to 1:1000. To carry out the screen, serum samples were first diluted to 1:10, and then preabsorbed with lysates of *E. coli* that had been transfected with naked vector, and the serum samples were then diluted to the levels described supra. The final dilutions were incubated overnight at room temperature with nitrocellulose membranes containing phage plaques, at a density of 4-5000 plaque forming units ("pfus") per 130 mm plate.

Nitrocellulose filters were washed, and incubated with alkaline phosphatase conjugated, goat anti-human Fcγ secondary antibodies, and reactive phage plaques were visualized via incubation with 5-bromo-4-chloro-3-indolyl phosphate and nitroblue tetrazolium.

This procedure was also carried out on a normal testicular cDNA library, using a 1:200 serum dilution.

A total of $1.12 \times 10^6$ pfus were screened in the breast cancer cDNA library, and 38 positive clones were identified. With respect to the testicular library, $4 \times 10^5$ pfus were screened, and 28 positive clones were identified.

Additionally, $8 \times 10^5$ pfus from the BR11 cDNA library were screened using the pooled serum described. Of these, 23 were positive.

The positive clones were subcloned, purified, and excised to forms suitable for insertion in plasmids. Following amplification of the plasmids, DNA inserts were evaluated via restriction mapping (EcoRI-XbaI), and clones which represented different cDNA inserts were sequenced using standard methodologies.

If sequences were identical to sequences found in GenBank, they were classified as known genes, while sequences which shared identity only with ESTs, or were identical to nothing in these data bases, were designated as unknown genes. Of the clones from the breast cancer library which were positive with autologous serum, 3 were unknown genes. Of the remaining 35, 15 were identical to either NY-ESO-1, or SSX2, two known members of the CT antigen family described supra, while the remaining clones corresponded to 14 known genes. Of the testicular library, 12 of the clones were SSX2.

The NY-ESO-1 antigen was not found, probably because the commercial library that was used had been size fractionated to have an average length of 1.5 kilobases, which is larger than full length NY-ESO-1 cDNA which is about 750 base pairs long.

With respect to the screening carried out with pooled, allogeneic sera, four of the clones were NY-ESO-1. No other CT antigens were identified. With the exception of NY-ESO-1, all of the genes identified were expressed universally in normal tissue.

A full listing of the isolated genes, and their frequency of occurrence follows, in tables 1, 2 and 3. Two genes were found in both the BR 11 and testicular libraries, i.e., poly (ADP-ribose) polymerase, and tumor suppression gene ING1. The poly (ADP-ribose) polymerase gene has also been found in colon cancer libraries screened via SEREX, as is disclosed by Scanlan, et al., *Int. J. Cancer*, 76:652-58 (1998) when the genes identified in the screening of the BR11 cDNA library by autologous and allogeneic sera were compared, NY-ESO-1 and human keratin.

TABLE 1

SEREX-defined genes identified by autologous screening of BR11 cDNA library

| Gene group | No. of clones | Comments | Expression |
|---|---|---|---|
| CT genes | 10 | NY-ESO-1 | tumor, testis |
|  | 5 | SSX2 | tumor, testis |
| Non-CT genes | 5 | Nuclear Receptor Co-Repressor | ubiquitous |
|  | 4 | Poly(ADP-ribose) polymerase | ubiquitous |
|  | 2 | Adenylosuccinatelyase | ubiquitous |
|  | 2 | cosmid 313 (human) | ESTs: muscle, brain, breast |
|  | 1 | CD 151 (transmembrane protein) | ubiquitous |
|  | 1 | Human HRY Gen | RT-PCR: multiple normal tissues |
|  | 1 | Alanyl-t-RNA-Synthetase | ubiquitous |
|  | 1 | NAD($^+$) ADP-Ribosyltransferase | ubiquitous |
|  | 1 | Human keratin 10 | ESTs: multiple normal tissues |
|  | 1 | Human EGFR kinase substrate | ubiquitous |
|  | 1 | ING 1 Tumor suppressor gene | RT-PCR: multiple normal tissues |
|  | 1 | Unknown gene, NCI_CGAP_Pr12 cDNA clone | ESTs: pancreas, liver, spleen, uterus |
|  | 1 | Unknown gene | ESTs: multiple normal tissues |
|  | 1 | Unknown gene | RT-PCR: multiple normal tissues |

TABLE 2

SEREX-defined genes identified by allogeneic screening of BR11 cDNA library

| Gene group | No. of clones | Comments | Expression |
|---|---|---|---|
| CT genes | 4 | NY-ESO-1 | tumor, testis |
| Non-CT genes | 6 | zinc-finger helicase | ESTs: brain, fetal heart, total fetus |
|  | 4 | Acetoacetyl-CoA-thiolase | ubiquitous |
|  | 3 | KIAA0330 gene | ESTs: multiple normal tissues |
|  | 2 | U1snRNP | ubiquitous |
|  | 1 | Human aldolase A | ubiquitous |
|  | 1 | Retinoblastoma binding protein 6 | ESTs: tonsils, fetal brain, endothelial cells, brain |
|  | 1 | α2-Macroglobulin receptor associated protein | ubiquitous |
|  | 1 | Human Keratin 10 | ESTs: multiple normal tissues |

TABLE 3

SEREX-defined genes identified by screening
of a testicular cDNA library with BR11 serum

| Gene group | No. of clones | Comments | Expression |
|---|---|---|---|
| CT genes: | 12 | SSX2 | tumor, testis |
| Non-CT genes: | 3 | Rho-associated coiled-coil forming protein | ubiquitous |
| | 3 | Poly(ADP-ribose) polymerase | ubiquitous |
| | 3 | Gene from HeLa cell, similar to TITIN | ubiquitous |
| | 2 | Gene from parathyroid tumor | RT-PCR: multiple normal tissues |
| | 1 | Transcription termination factor I-interacting peptide 21 | ubiquitous |
| | 1 | Gene from fetal heart | ESTs: multiple normal tissues |
| | 1 | ING 1 tumor suppressor gene | RT-PCR: multiple normal tissues |
| | 1 | KIAA0647 CdnA | ESTs: multiple normal tissues |
| | 1 | KIAA0667 cDNA | ESTs: multiple normal tissues |

Example 2

The mRNA expression pattern of the cDNAs identified in example 1, in both normal and malignant tissues, was studied. To do this, gene specific oligonucleotide primers were designed which would amplify cDNA segments 300-600 base pairs in length, using a primer melting temperature of 65-70° C. The primers used for amplifying MAGE-1, 2, 3 and 4, BAGE, NY-ESO-1, SCP1, and SSX1, 2, 3, 4 and 5 were known primers, or were based on published sequences. See Chen, et al. supra; Tureci, et al., *Proc. Natl. Acad. Sci. USA,* 95:5211-16 (1998). Gure, et al., *Int. J. Cancer,* 72:965-71 (1997); Chen, et al., *Proc. Natl. Acad. Sci. USA,* 91:1004-1008 (1994); Gaugler, et al., *J. Exp. Med.,* 179:921-930 (1994), dePlaen, et al., *Immunogenetics,* 40:360-369 (1994), all of which are incorporated by reference. RT-PCR was carried out for 35 amplification cycles, at an annealing temperature of 60° C. Using this RT-PCR assay, the breast cancer tumor specimen was positive for a broad range of CT antigens, including MAGE-1, 3 AND 4, BAGE, SSX2, NY-ESO-1 and CT7. The known CT antigens SCP-1, SSX1, 4 and 5 were not found to be expressed.

An additional set of experiments were carried out, in which the seroreactivity of patient sera against tumor antigens was tested. Specially, ELISAs were carried out, in accordance with Stockert, et al., *J. Exp. Med.,* 187:1349-1354 (1998), incorporated by reference, to determine if antibodies were present in the patient sera. Assays were run for MAGE-1, MAGE-3, NY-ESO-1, and SSX2. The ELISAs were positive for NY-ESO-1 and SSX2, but not the two MAGE antigens.

Example 3

Two clones (one from the breast cancer cDNA library and one from the testicular library), were identified as a gene referred to as ING1, which is a tumor suppressor gene candidate. See Garkavtsev, et al., *Nature,* 391:295-8 (1998), incorporated by reference. The sequence found in the breast cancer library, differed from the known sequence of ING1 at six residues, i.e., positions 818, 836, 855, 861, 866 and 874. The sequence with the six variants is set forth at SEQ ID NO: 1. The sequence of wild type ING1 is set out at SEQ ID NO: 2.

To determine if any of these differences represented a mutation in tumors, a short, PCR fragment which contained the six positions referred to supra was amplified from a panel of allogeneic normal tissue, subcloned, amplified, and sequenced following standard methods.

The results indicated that the sequences in the allogeneic tissues were identical to what was found in tumors, ruling out the hypothesis that the sequence differences were a tumor associated mutation. This conclusion was confirmed, using the testicular library clone, and using restriction analysis of ING1 cDNA taken from normal tissues. One must conclude, therefore, that the sequence information provided by Garkavtsev, et al., supra, is correct.

Example 4

Additional experiments were carried out to determine whether genetic variations might exist in the 5' portion of the ING1 gene, which might differ from the 5' portion of the clone discussed supra (SEQ ID NO: 1). In a first group of experiments, attempts were made to obtain full length ING1 cDNA from both the breast tumor library, and the testicular library. SEQ ID NO: 1 was used as a probe of the library, using standard methods.

Four clones were isolated from the testicular library and none were isolated from the breast cancer library. The four clones, following sequencing, were found to derive from three transcript variants. The three variants were identical from position 586 down to their 3' end, but differed in their 5' regions, suggesting alternatively spliced variants, involving the same exon-intron junction. All three differed from the sequence of ING1 described by Garkavtsev, et al., in *Nat. Genet.,* 14:415-420 (1996). These three variants are set out as SEQ ID NOS: 1, 3 and 4.

All of the sequences were then analyzed. The ORFs of SEQ ID NOS: 2, 1 and 4 (SEQ ID NO: 2 is the originally disclosed, ING1 sequence), encode polypeptides of 294, 279 and 235 amino acids, of which 233 are encoded by the 3' region common to the three sequences. These putative sequences are set out as SEQ ID NOS: 19, 5, and 7. With respect to SEQ ID NO: 3, however, no translational initiation site could be identified in its 5' region.

Example 5

The data regarding SEQ ID NO: 3, described supra, suggested further experiments to find additional ORFs in the 5-end of variant transcripts of the molecule. In order to determine this, 5'-RACE-PCR was carried out using gene specific and adapted specific primers, together with commercially available products, and standard methodologies.

The primers used for these experiments were:

```
            (SEQ ID NOS: 9 and 10), for SEQ ID NO: 1
CACACAGGATCCATGTTGAGTCCTGCCAACGGCGTGGTCGTGGTTGCTGG
ACGCG;

(SEQ ID NOS: 11 and 12), for SEQ ID NO: 3
CCCAGCGGCCCTGACGCTGTCCGTGGTCGTGGTTGCTGGACGCG;
and (SEQ ID NOS: 13 and 14), for SEQ ID NO: 4
GGAAGAGATAAGGCCTAGGGAAGCGTGGTCGTGGTTGCTGGACGCG.
```

Cloning and sequencing of the products of RACE PCR showed that the variant sequence of SEQ ID NO: 4 was 5' to SEQ ID NO: 3, and that full length cDNA for the variant SEQ ID NO: 3 contained an additional exon 609 nucleotides long, positioned between SEQ ID NO: 3 and the shared, 3' sequence referred to supra. This exon did not include an ORF. The first available initiation site would be an initial methionine at amino acid 70 of SEQ ID NO: 1. Thus, if expressed, SEQ ID NO: 3 would correspond to a molecule with a 681 base pair, untranslated 5' end and a region encoding 210 amino acids (SEQ ID NO: 6).

Example 6

The presence of transcript variants with at least 3 different transcriptional initiation sites, and possibly different promoters, suggested that mRNA expression might be under different, tissue specific regulation.

To determine this, variant-specific primers were synthesized, and RT-PCR was carried out on a panel of tissues, using standard methods.

SEQ ID NO: 1 was found to be expressed universally in all of the normal breast, brain and testis tissues examined, in six breast cancer lines, and 8 melanoma cell lines, and in cultured melanocytes. SEQ ID NO: 3 was found to be expressed in four of the six breast cancer lines, normal testis, liver, kidney, colon and brain. SEQ ID NO: 4 was only found to be expressed by normal testis cells and weakly in brain cells.

Example 7

A further set of experiments were carried out to determine if antibodies against ING1 were present in sera of normal and cancer patients. A phase plaque immunoassay of the type described supra was carried out, using clones of SEQ ID NO: 1 as target. Of 14 allogeneic sera taken from breast cancer patients, two were positive at 1:200 dilutions. All normal sera were negative.

Example 8

The BR11 cDNA library described supra was then screened, using SEQ ID NO: 1 and standard methodologies. A 772 base pair cDNA was identified, which was different from any sequences in the data banks consulted. The sequence of this cDNA molecule is set out at SEQ ID NO: 8.

The cDNA molecule set forth as SEQ ID NO: 1 was then used in Southern blotting experiments. In brief, genomic DNA was isolated from normal human tissue, digested with BamHI or Hind III, and then separated onto 0.7% agarose gel, blotted onto nitrocellulose filters, and hybridized using 32P labelled SEQ ID NO: 1, at high stringency conditions (aqueous buffer, 65° C.). The probes were permitted to hybridize overnight, and then exposed for autoradiography. Two hybridizing DNA species were identified, i.e., SEQ ID NOS: 1 and 8.

Example 9

The cDNA molecule set forth in SEQ ID NO: 8 was then analyzed. 5'-RACE PCR was carried out using normal fetus cDNA. Full length cDNA for the molecule is 772 base pairs long, without the poly A tail. It shows strong homology to SEQ ID NO: 1, with the strongest homology in the 5' two-thirds (76% identity over nucleotide 1-480); however, the longest ORF is only 129 base pairs, and would encode a polypeptide 42 amino acids long which was homologous to, but much shorter than, the expected expression product of SEQ ID NO: 1.

In addition to the coding region, SEQ ID NO: 8 contains 203 base pairs of 5'-untranslated region, and 439 base pairs of 3'-untranslated region.

RT-PCR assays were carried out, as described supra. All of the normal tissues tested, including brain, colon, testis, tissue and breast, were positive for expression of this gene. Eight melanoma cell lines were tested, of which seven showed varying levels of expression, and one showed no expression. Six breast cancer cell lines were tested, of which four showed various levels of expression, and two showed no expression.

Example 10

An additional breast cancer cDNA library, referred to as "BR17-128", was screened, using autologous sera. A cDNA molecule was identified.

Analysis of the sequence suggested that it was incomplete at the 5' end. To extend the sequence, a testicular cDNA library was screened with a nucleotide probe based upon the partial sequence identified in the breast cancer library. An additional 1200 base pairs were identified following these screenings. The 2030 base pairs of information are set forth in SEQ ID NO: 15.

The longest open reading frame is 1539 base pairs, corresponding to a protein of about 59.15 kilodaltons, and 512 amino acids. The deduced amino acid sequence is set forth at SEQ ID NO: 16.

RT-PCR was then carried out using the following primers:

```
                                        (SEQ ID NOS: 17 and 18)
CACACAGGATCCATGCAGGCCCCGCACAAGGAGCACACAAAGCTTCTAGG

ATTTGGCACAGCCAGAG
```

Strong signals were observed in normal testis and breast tissue, and weak expression was observed in placenta.

No expression was found in normal brain, kidney, liver, colon, adrenal, fetal brain, lung, pancreas, prostate, thymus, uterus, and ovary tissue of tumor cell lines tested, 2 of the breast cancer lines were strongly positive and two were weakly positive. Of melanoma two of 8 were strongly positive, and 3 were weakly positive. Of lung cancer cell lines, 4 of 15 were strongly positive, and 3 were weakly positive.

When cancer tissue specimens were tested, 16 of 25 breast cancer samples were strongly positive, and 3 additional samples were weakly positive. Two of 36 melanoma samples were positive (one strong, one weak). All other cancer tissue samples were negative.

When Northern blotting was carried out, a high molecular weight smear was observed in testis, but in no other tissues tested.

Example 11

Further experiments were carried out using the tumor sample referred to in example 10, supra. This sample was derived from a subcutaneous metastasis of a 60 year old female breast cancer patient. Total RNA was extracted, as described supra. Following the extraction, a cDNA library was constructed in λ-ZAP expression vectors, also as described supra. Screening was carried out, using the protocol set forth in example 1. A total of 7×105 pfus were screened. Fourteen reactive clones were identified, purified, and sequenced. The sequences were then compared to published sequences in GenBank and EST databases. These analyses indicated that the clones were derived from seven distinct genes, two of which were known, and five unknown. The two known genes were "PBK-1" (three clones), and TI-227 (one clone). These are universally expressed genes, with the libraries referred to supra showing ESTs for these genes from many different tissues.

With respect to the remaining 10 clones, six were derived from the same gene, referred to hereafter as "NY-BR-1." Three cDNA sequences were found in the EST database which shared identity with the gene. Two of these (AI 951118 and AW 373574) were identified as being derived from a breast cancer library, while the third (AW 170035), was from a pooled tissue source.

Example 12

The distribution of the new gene NY-BR-1 referred to supra was determined via RT-PCR. In brief, NY-BR-1 gene specific oligonucleotide primers were designed to amplify cDNA segments 300-600 base pairs in length, with primer melting temperatures estimated at 65-70° C.

The RT-PCR was then carried out over 30 amplification cycles, using a thermal cycler, and an annealing temperature of 60° C. Products were analyzed via 1.5% gel electrophoresis, and ethidium bromide visualization. Fifteen normal tissues (adrenal gland, fetal brain, lung, mammary gland, pancreas, placenta, prostate, thymus, uterus, ovary, brain, kidney, liver, colon and testis) were assayed. The NY-BR-1 clone gave a strong signal in mammary gland and testis tissue, and a very faint signal in placenta. All other tissues were negative. The other clones were expressed universally, based upon comparison to information in the EST database library, and were not pursued further.

The expression pattern of NY-BR-1 in cancer samples was then tested, by carrying out RT-PCR, as described supra, on tumor samples.

In order to determine the expression pattern, primers:

```
caaagcagag cctcccgaga ag     (SEQ ID NO: 20)
and cctatgctgc tcttcgattc ttcc   (SEQ ID NO: 21)
``` were used.

Of twenty-five breast cancer samples tested, twenty two were positive for NY-BR-1. Of these, seventeen gave strong signals, and five gave weak to modest signals.

An additional 82 non-mammary tumor samples were also analyzed, divided into 36 melanoma, 26 non small cell lung cancer, 6 colon cancer, 6 squamous cell carcinoma, 6 transitional cell carcinoma, and two leiyomyosarcomas. Only two melanoma samples were positive for NY-BR-1 expression.

The study was then extended to expression of NY-BR-1 in tissue culture. Cell lines derived from breast tumor, melanoma, and small cell lung cancer were studied. Four of six breast cancer cells were positive (two were very weak), four of eight melanoma (two very weak), and seven of fourteen small cell lung cancer lines (two very weak) were positive.

Example 13

Studies were continued in order to determine the complete cDNA sequence for NY-BR-1. First, the sequences of the six clones referred to supra were compiled using standard methods, to produce a nucleotide sequence 1464 base pairs long. Analysis of the open reading frame showed a continuous ORF throughout, indicating that the compiled sequence is not complete.

Comparison of the compiled sequence with the three EST library sequences referred to supra allowed for further extension of the sequence. The EST entry AW170035 (446 base pairs long) overlapped the compiled sequence by 89 base pairs at its 5' end, permitting extension of the sequence by another 357 base pairs. A translational terminal codon was identified in this way, leading to a molecule with a 3'-untranslated region 333 base pairs long. The 5' end of the molecule was lacking, however, which led to the experiments described infra.

Example 14

In order to determine the missing, 5' end of the clone described supra, a commercially available testis cDNA expression library was screened, using a PCR expression product of the type described supra, as a probe. In brief, 5×10⁴ pfus per 150 mm plate were transferred to nitrocellulose membranes, which were then submerged in denaturation solution (1.5M NaCl and 0.5 M NaOH), transferred to neutralization solution (1.5 M NaCl and 0.5M Tris-HCl), and then rinsed with 0.2M Tris-HCl, and 2×SSC. Probes were labelled with 32P and hybridization was carried out at high stringency conditions (i.e., 68° C., aqueous buffer). Any positive clones were subcloned, purified, and in vivo excised to plasmid PBK-CMV, as described supra.

One of the clones identified in this way included an additional 1346 base pairs at the 5' end; however, it was not a full length molecule. A 5'-RACE-PCR was carried out, using commercially available products. The PCR product was cloned into plasmid vector pGEMT and sequenced. The results indicated that cDNA sequence extended 1292 base pairs further, but no translation initiation site could be determined, because no stop codons could be detected. It could be concluded, however, that the cDNA of the NY-BR17 clone comprises at least 4115 nucleotides, which are presented as SEQ ID NO: 22. The molecule, as depicted, encodes a protein at least about 152.8 kDA in molecular weight. Structurally, there are 99 base pairs 5' to the presumed translation initiation site, and an untranslated segment 333 base pairs long at the 3' end. The predicted amino acid sequence of the coding region for SEQ ID NO: 22 is set out at SEQ. ID NO: 23.

SEQ ID NO: 23 was analyzed for motifs, using the known search programs PROSITE and Pfam. A bipartite nuclear localization signal motif was identified at amino acids 17-34, suggesting that the protein is a nuclear protein. Five tandem ankyrin repeats were identified, at amino acids 49-81, 82-114, 115-147, 148-180 and 181-213. A bZIP site (i.e., a DNA binding site followed by a leucine zipper motif) was found at amino acid positions 1077-1104, suggesting a transcription factor function. It was also observed that three repetitive elements were identified in between the ankyrin repeats and the bZIP DNA binding site. To elaborate, a repetitive element 117 nucleotides long is trandemly repeated 3 times, between amino acids 459-815. The second repetitive sequence, consisting of 11 amino acids, repeats 7 times between amino acids 224 and 300. The third repetitive element, 34 amino acids long, is repeated twice, between amino acids 301-368.

Example 15

The six clones described supra were compared, and analysis revealed that they were derived from two different splice variants. Specifically, two clones, referred to as "BR17-8" and "BR 17-44a", contain one more exon, of 111 base pairs (nucleotides 3015-3125 of SEQ ID NO: 22), which encodes amino acids 973-1009 of SEQ ID NO: 23, than do clones BR 17-1a, BR17-35b and BR17-44b. The shortest of the six clones, BR17-128, starts 3' to the additional exons. The key structural elements referred to supra were present in both splice variants, suggesting that there was no difference in biological function.

The expression pattern of the two splice variants was assessed via PT-PCR, using primers which spanned the 111 base pair exon referred to supra.

The primers used were:

```
aatgggaaca agagctctgc ag      (SEQ ID NO: 24)
and gggtcatctg aagttcagca ttc     (SEQ ID NO: 25)
```

Both variants were expressed strongly in normal testis and breast. The longer variant was dominant in testis, and the shorter variant in breast cells. When breast cancer cells were tested, co-typing of the variant was observed, (7 strongly, 2 weakly positive, and 1 negative), with the shorter variant being the predominant form consistently.

Example 16

The frequency of antibody response against NY-BR-1 in breast cancer patients was tested. To do this, a recombinant protein consisting of amino acids 993-1188 of SEQ ID NO: 23 was prepared. (This is the protein encoded by clone BR 17-128, referred to supra). A total of 140 serum samples were taken from breast cancer patients, as were 60 normal serum samples. These were analyzed via Western blotting, using standard methods.

Four of the cancer sera samples were positive, including a sample from patient BR17. All normal sera were negative.

An additional set of experiments was then carried out to determine if sera recognized the portion of NY-BR-1 protein with repetitive elements. To do this, a different recombinant protein, consisting of amino acids 405-1000 was made, and tested in Western blot assays. None of the four antibody positive sera reacted with this protein indicating that an antibody epitope is located in the non-repetitive, carboxy terminal end of the molecule.

Example 17

The screening of the testicular cDNA library referred to supra resulted, inter alia, in the identification of a cDNA molecule that was homologous to NY-BR-1. The molecule is 3673 base pairs in length, excluding the poly A tail. This corresponded to nucleotides 1-3481 of SEQ ID NO: 22, and showed 62% homology thereto. No sequence identity to sequences in libraries was noted. ORF analysis identified an ORF from nucleotide 641 through the end of the sequence, with 54% homology to the protein sequence of SEQ. ID NO: 23. The ATG initiation codon of this sequence is 292 base pairs further 3' to the presumed initiation codon of NY-BR-1, and is preceded by 640 untranslated base pairs at its 5' end. This 640 base pair sequence includes scattered stop codons. The nucleotide sequence and deduced amino acid sequence are presented as SEQ ID NOS: 26 and 27, respectively.

RT-PCR analysis was carried out in the same way as is described supra, using primers:

```
tctcatagat gctggtgctg atc     (SEQ ID NO: 28)
and cccagacatt gaattttggc agac.   (SEQ ID NO: 29)
```

Tissue restricted mRNA expression was found. The expression pattern differed from that of SEQ ID NO: 22. In brief, of six normal tissues examined, strong signals were found in brain and testis only. There was no or weak expression in normal breast tissues, and kidney, liver and colon tissues were negative. Eight of ten 10 breast cancer specimens tested supra were positive for SEQ. ID NO: 26. Six samples were positive for both SEQ. ID NO: 22 and 26, one for SEQ. ID NO: 22 only, two for the SEQ. ID NO: 26 only, and one was negative for both.

Example 18

Recently, a working draft of the human genome sequence was released. This database was searched, using standard methods, and NY-BR-1 was found to have sequence identity with at least three chromosome 10 clones, identified by Genbank accession numbers AL157387, AL37148, and AC067744. These localize NY-BR-1 to chromosome 10 p11.21-12.1.

The comparison of NY-BR-1 and the human genomic sequence led to definition of the exon-intron organization of NY-BR-1. In brief, the coding region of the gene contains essentially 19 structurally distinct exons with at least 2 exons encoding 3' untranslated regions. Detailed exon-intron junction information is described at Genbank AF 269081.

The six ankyrin repeats, referred to supra, are all found within exon 7. The 357 nucleotide repeating unit is composed of exons 10-15. The available genomic sequences are not complete, however, and only one of the three copies was identified, suggesting that DNA sequences between exons 5 and 10 may be duplicated and inserted in tandem, during genetic evolution. In brief, when the isolated NY-BR-1 cDNA clone was analyzed, three complete and one incomplete copy of the repeating units were found. The exon sequences can be expressed as exons 1-2-3-4-5-6-7-8-9-(10-11-12-13-14-15)-(10A-11A-12A-13A-14A-15A)-(10B-11B-12B-13B-14B-15B)-(10C-11C-12C-13C-14C)-16-17-18-19-20-21, wherein A, B & C are inexact copies of exon 10-15 sequences. Cloned, NY-BR-1 cDNA has 38 exons in toto.

It was noted, supra, that the sequence of NY-BR-1 cDNA was not complete at the 5' end. A genomic sequence (Genbank AC067744), permitted extension of the 5' end. This extended sequence is set forth in SEQ ID NO: 31. It consists of 4194 base pairs of coding sequence, plus a 2088 base pair segment 3' to the coding segment, which is untranslated. (This excludes the poly A tail). As remarked upon previously, this sequence contains a bipartite nuclear localization signal, 5 ankyrin repeats, and a b zip site. Translation of the 5' genomic sequence led to the identification of a new translation initiation site, 168 base pairs upstream of the previously predicted ATG initiation codon. This resulted in an NY-BR-1 polypeptide including 1397 amino acids which is 56 amino acid residues longer, at the N-terminus, as compared to SEQ ID NO: 23. The additional amino acids are: MEEISAAAVKV-VPGPERPSPFSQLVYTSNDSYIVHSGDL-RKIHKAASRGQVRKLE K (SEQ ID NO: 30). These amino acids are positioned N-terminal to SEQ ID NO: 23, in SEQ ID NO: 32.

Example 19

Reference was made, supra, to the two difference splice variants of NY-BR-1. Comparison of the splice variants with the genomic sequence confirmed that an alternate splicing event, with the longer variant incorporating part of intron 33 into exon 34 (i.e., exon 17 of the basic exon/intron framework described supra), had occurred.

Key structural elements that were predicted in NY-BR-1, described supra, are present in both variants, suggesting that there is no difference in biological function, or subcellular location.

Example 20

As with NY BR-1, the variant NY-BR-1.1, described supra, was screened against the working draft of the human genomic sequence. One clone was found with sequence identity, i.e., GenBank AL359312, derive from chromosome 9. Thus, NY-BR-1 and NY-BR-1.1 both appear to be functioning genes, on two different chromosomes. The Genbank sequences referred to herein does not contain all of NY-BR-1.1, which precludes defining exon-intron structure. Nonetheless, at least 3 exons can be defined, which correspond to exons 16-18 of the NY-BR-1 basic framework. Exon-intron junctions are conserved.

Example 21

A series of peptides were synthesized, based upon the amino acid sequence of NY-BR-1, as set forth in SEQ ID NO: 23 and the concatenation of SEQ ID NOS: 30 & 23, as described supra and set forth at SEQ ID NO: 32. These were then tested for their ability to bind to HLA-A2 molecules and to stimulate CTL proliferation, using an ELISPOT assay. This assay involved coating 96-well, flat bottom nitrocellulose plates with 5 ug/ml of anti-interferon gamma antibodies in 100 ul of PBS per well, followed by overnight incubation. Purified CD8+ cells, which had been separated from PBL samples via magnetic beads coated with anti-CD8 antibodies were then added, at 1×105 cells/well, in RPMI 1640 medium, that had been supplemented with 10% human serum, L-asparagine (50 mg/l), L-arginine (242 mg/l), L-glutamine (300 mg/l), together with IL-2 (2.5 ng/ml), in a final volume of 100 ul. CD8+ effector cells were prepared by presensitizing with peptide, and were then added at from 5×103 to 2×104 cells/well. Peptides were pulsed onto irradiated T2 cells at a concentration of 10 ug/ml for 1 hour, washed and added to effector cells, at 5×104 cells/well. The plates were incubated for 16 hours at 37° C., washed six times with 0.05% Tween 20/PBS, and were then supplemented with biotinylated, anti-interferon gamma specific antibody at 0.5 ug/ml. After incubation for 2 hours at 37° C., plates were washed, and developed with commercially available reagents, for 1 hour, followed by 10 minutes of incubation with dye substrate. Plates were then prepped for counting, positives being indicated by blue spots. The number of blue spots/well was determined as the frequency of NY-ESO-1 specific CTLs/well.

Experiments were run, in triplicate, and total number of CTLs was calculated. As controls, one of reagents alone, effector cells alone, or antigen presenting cells alone were used. The difference between the number of positives in stimulated versus non-stimulated cells, was calculated as the effective number of peptide specific CTLs above background. Three peptides were found to be reactive, i.e.:

LLSHGAVIEV (amino acids 102-111 of SEQ ID NO: 23, 158-167 of SEQ ID NO: 32)

SLSKILDTV (amino acids 904-912 of SEQ ID NO: 23, 960-968 of SEQ ID NO: 32)

SLDQKLFQL (amino acids 1262-1270 of SEQ ID NO: 23, 1318-1326 of SEQ ID NO: 32).

The complete list of peptides tested, with reference to their position in SEQ ID NO: 23, follows:

| Peptide | Position |
|---|---|
| FLVDRKVCQL | 35-43 |
| ILIDSGADI | 68-76 |
| AVYSEILSV | 90-98 |
| ILSVVAKLL | 95-103 |
| LLSHGAVIEV | 102-111 |
| KLLSHGAVI | 101-109 |
| FLLIKNANA | 134-142 |
| MLLQQNVDV | 167-175 |
| GMLLQQNVDV | 166-175 |
| LLQQNVDVFA | 168-177 |
| IAWEKKETPV | 361-370 |
| SLFESSAKI | 430-438 |
| CIPENSIYQKV | 441-450 |
| KVMEINREV | 449-457 |
| ELMDMQTFKA | 687-696 |
| ELMDMQTFKA | 806-815 |
| SLSKILDTV | 904-912 |
| KILDTVHSC | 907-915 |
| ILNEKIREEL | 987-996 |
| RIQDIELKSV | 1018-1027 |
| YLLHENCML | 1043-1051 |
| CMLKKEIAML | 1049-1058 |
| AMLKLELATL | 1056-1065 |
| KILKEKNAEL | 1081-1090 |
| VLIAENTML | 1114-1122 |
| CLQRKMNVDV | 1174-1183 |
| KMNVDVSST | 1178-1186 |
| SLDQKLFQL | 1262-1270 |
| KLFQLQSKNM | 1266-1275 |
| FQLQSKNMWL | 1268-1277 |
| QLQSKNMWL | 1269-1277 |
| NMWLQQQLV | 1274-1282 |
| WLQQQLVHA | 1276-1284 |
| KITIDIHFL | 1293-1301 |

Example 22

Expression of the full length NY-BR-1 molecule was analyzed, by determining the presence of mRNA, in various normal and tumor tissue samples.

RT-PCR assays were carried out, as described in examples 5 & 9, on a variety of tissue samples.

Expression on the mRNA level was found in normal breast and testis tissue, but in none of normal adrenal gland, fetal brain, lung, pancreatic, placental, prostate, thymus, uterine, ovarian, adult brain, kidney, liver or colon tissue.

With respect to cancer tissue samples, 19/34 breast cancer samples were positive, as were 9/34 prostate cancer biopsies.

Example 23

These experiments describe work which identified and verified two, naturally processed T cell epitopes that consist of amino acid sequences found in NY-BR-1.

Sequences encoding NY-BR-1 were excised from plasmid pQE9, via standard restriction enzyme digestion, and were cloned into BamHI-Hind III sites of commercially available plasmid pcDNA31 (−).

The resulting vectors were then transfected into COS-7 cells. To accomplish this, $2\times10^4$ COS-7 cells were admixed with 150 ng of the construct described supra, and 150 ng of plasmid pcDNA-AmpI, which contained cDNA encoding HLA-A2. The standard DE AE-dextran chloroquine method was used. Transfectants were then incubated at 37° C. for 48 hours, and then tested in a T cell stimulation assay, after 24 hours, as described infra.

The transfectants were tested to determine if they could stimulate production of TNF-α by CTLs specific for complexes of HLA-A2 molecules and one of the peptides described supra. The CTLs used were CD8$^+$ T cell clones. "NW 1100-CTL-7," "NW1100-CTL39," and "NW1100-CTL43." These three CD8$^+$ T cell clones had been generated via repeated in vitro stimulation with either LLSHGAVIEV or SLSKILDTV, using standard methods.

To test if the transfectants stimulated the CD8$^+$ cells, 5000 of these CD8$^+$ cells, in 100 μl RPMI supplemented with 10% human serum, and 25 U/ml of recombinant human IL-2 were added to micowells containing the transfectants. After 24 hours, 50 μl samples of supernatant were collected, and TNFα content was determined by testing cytotoxicity against WEHI 164 clone 13 cells, in an MTT colorimetric assay, which is a standard method for showing TNFα production.

Figure 2:
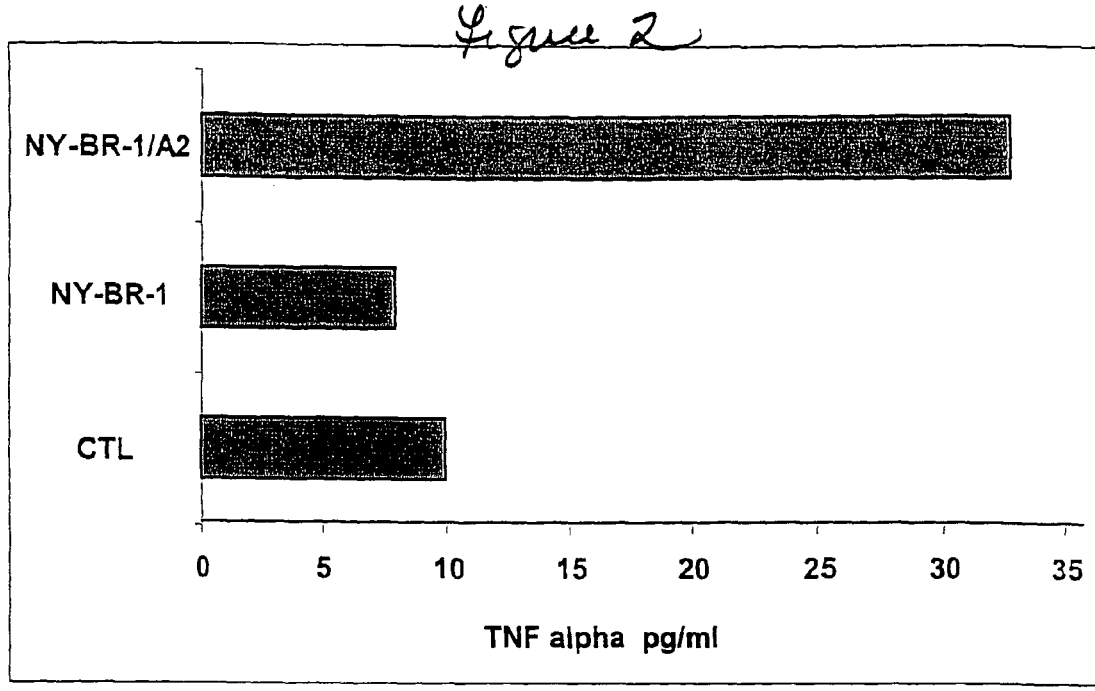
Figure 3:
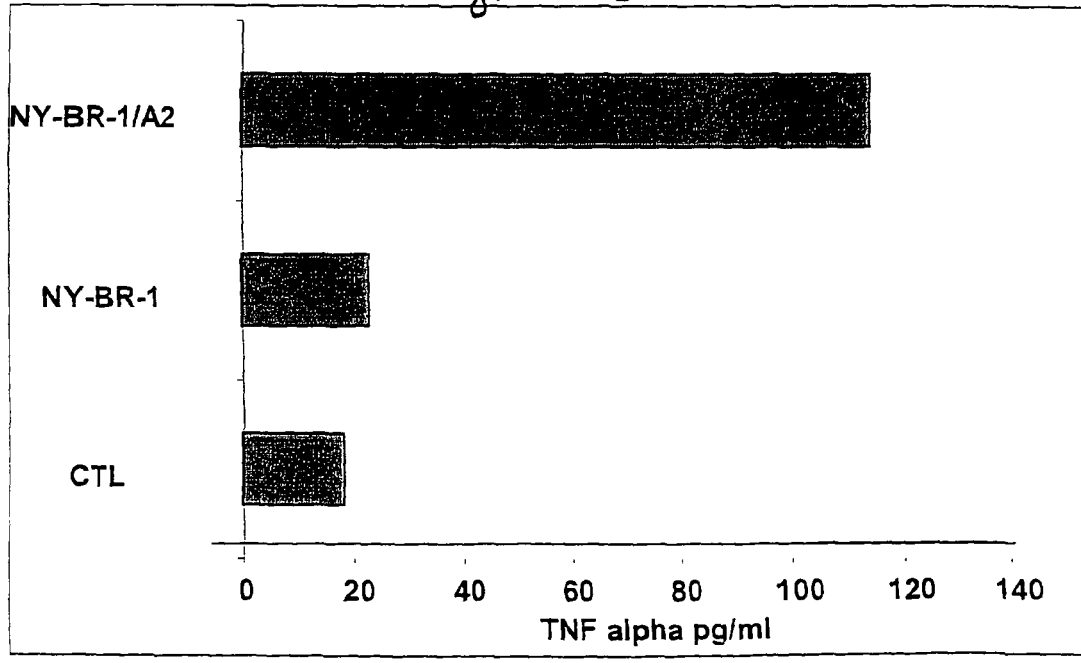

The results are shown in FIGS. 1, 2 and 3. Briefly, both peptide/HLA-A2 complexes were recognized by CD8$^+$ T cells obtained from breast cancer patient identified as NW-1100. These results indicate that the two peptides are, in fact, naturally processed.

Example 24

This example describes studies carried out in NY-BR-1 positive cancer patients, to determine sequences which contained epitopes which were in vivo targets of CD4$^+$ and CD8$^+$ cells.

Tumor biopsies/resection specimens of patients with breast- and prostate-cancer, which were snap frozen in liquid nitrogen, were tested for the expression of NY-BR-1 by RT-PCR using the following primers: 5'-CAAAGCAGAGC-CTCCCGAGAAG-3(SEQ ID NO:33)' and 5'-CCTATGCT-GCTCTTCGATTCTTCC-3 (SEQ ID NO:34)'.

CD4$^+$ and CD8$^+$ T lymphocytes were separated from PBMC of NY-BR-1 positive patients by magnetic beads (MiniMACS) and seeded into 48-well plates at a concentration of 2.5-5×10$^5$ cells per well in RPMI medium 1640 supplemented with 10% human serum, L-asparagine (50 mg/l), L-arginine (242 mg/l), and L-glutamine (300 mg/l). PBMC depleted of T cells were used as antigen presenting cells. After irradiation, these cells were incubated with 39 single peptides (10 μg/ml) spanning amino acids 1004-1397 of NY-BR-1(SEQ ID NO: 32) each of 18 amino acids in length and overlapping in 8 positions on each terminus, for 1 hour at room temperature and added to plates at a concentration of $1\times10^6$ cells per well. IL-2 and IL-4 (2.5 ng/ml and 50 U/ml, respectively) were added to CD4$^+$ T cell cultures, and IL-2 and IL-7 (2.5 ng/ml and 10 ng/ml, respectively) to CD8$^+$ T cells. Peptide specific T cell responses against the stimulating epitope were determined by IFN-gamma ELISPOT assays 6 to 12 days after presensitization.

Flat-bottomed, 96 well nitrocellulose plates were coated with IFN-γ mAb and incubated overnight at 4° C. After washing with PBS, the plates were blocked with 10% human AB serum for 1 hour at 37° C. Presensitized CD4$^+$ or CD8$^+$ T cells from ($1\times10^3$ to $5\times10^4$) and $5\times10^4$ peptide-pulsed APC (autologous Dendritic Cells or Epstein Barr Virus transfected B cells) were added to each well and incubated for 20 hours in RPMI medium 1640 lacking both IL-2 and human serum. Plates were then washed thoroughly with PBS to remove cells, and biotinylated IFN-γ mAbs were added to each well. After incubation for 2 hours at 37° C., the plates were washed and developed with streptavidin-alkaline phosphase for 1 hour at room temperature. After washing, substrate (5-bromo-4-chloro-3-indolyl phosphate/nitroblue tetrazolium) was added and incubated for 5 minutes. After final washes, plate membranes displayed dark-violet spots that were counted under the microscope.

Both CD4$^+$ and CD8$^+$ T cells were collected from twenty patients, who had been diagnosed with cancer and expressed NY-BR-1, as determined via the methods set forth supra. These CD4$^+$ and CD8$^+$ T cells were then analyzed for spontaneous NY-BR-1 specific, CD4$^+$ and CD8$^+$ responses.

Lymphocytes, which had been purified in accordance with the standard methods set forth supra, were presensitized with synthetic 18 mers which overlapped each other, and spanned amino acids 1104-1397 of SEQ ID NO: 32.

Following the presensitization, effector cell populations were tested for recognition of ELISPOT assays, with autologous, EBV transfected B cells, and T2 cell lines being used as the antigen presenting cells in the ELISPOT assays. ELISPOT assays were carried out as described supra.

A total of 39 peptides were tested. The sequences recognized by patient T-cells are shown in Table 5. Peptides which were recognized by CD8$^+$ cells included peptides consisting of amino acids 1214-1231, 1224-1241, 1264-1281, 1274-1291, and 1334-1351 of SEQ ID NO: 32, as set forth in Table 7. Further, analysis of the peptide defined by amino acids 1214-1231 showed that it was restricted to HLA-A2, because it was recognized when pulsed onto T2 cells. HLA-A2 is the only shared allele between T2 cells and patient 1.

CD4$^+$ cells reacted with peptides defined by amino acids 1011-1021, 1094-1111, 1124-1141, 1134-1151, 1164-1181, 1264-1281, 1364-1381, and 1374-1391, as set forth in Table 6.

This example shows that the sequences presented in Tables 5-7 contains the naturally occurring T-cell epitopes which, after being processed/degraded in the cell bind to the appropriate MHC molecule and the MHC-peptide complex being transported to the cells surface, are recognized by patient T-cells. The degradation pathways for MHC class I and II molecules for eventual presentation to either CD4 or CD8 T-cells are well known within the art (see for example Chapter 5 of Janeway et al. Immunobiology. The Immune System in Health and Disease. 5$^{th}$ Edition. Garland Publishing, New York. 2001).

TABLE 5

IDENTIFIED SEQUENCES CONTAINING CD4 AND CD8 T-CELL EPITOPES RECOGNIZED BY PATIENT T-CELLS. (ALL AMINO ACID SEQUENCE NUMBERING IS BY REFERENCE TO SEQ ID NO: 32)

| Patient | CD4 epitope | Sequence of CD4 epitope | CD8 epitope | Sequence of CD8 epitope |
|---|---|---|---|---|
| 1 | 1164-1181 | YSGQLKVLIAENTMLTSK | 1214-1231 | TSRKSQEPAFHIAGDACL |
|  |  |  | 1224-1241 | HIAGDACLQRKMNVDVSS |
|  |  |  | 1274-1291 | LRENTLVSEHAQRDQRET |
|  |  |  | 1334-1351 | QQQLVHAHKKADNKSKIT |
| 2 | 1124-1141 | QYQEKENKYFEDIKILKE |  |  |
|  | 1164-1181 | YSGQLKVLIAENTMLTSK |  |  |
| 3 | 1344-1361 | ADNKSKITIDIHFLERKM |  |  |
| 4 | 1014-1031 | ENQKVKWEQELCSVRLTL |  |  |
|  | 1264-1281 | KINLNYAGDALRENTLVS |  |  |
|  | 1344-1361 | ADNKSKITIDIHFLERKM |  |  |
|  | 1364-1381 | HLLKEKNEEIFNYNNHLK |  |  |
| 5 | 1254-1271 | SEAQRKSKSLKINLNLYAG |  |  |
| 6 | 1254-1271 | SEAQRKSKSLKILNLYAG |  |  |
| 7 | 1374-1391 | FNYNNHLKNRIYQYEKEK |  |  |
| 8 |  |  | 1264-1281 | KINLNYAGDALRENTLVS |
| 9 (healthy donor) | 1094-1111 | HENENYLLHENCMLKKEI |  |  |
|  | 1134-1151 | EDIKILKEKNAELQMTLK |  |  |

TABLE 6

NY-BR-1 PEPTIDES RECOGNIZED BY CD4+ T CELLS (ALL AMINO ACID INFORMATION IS BY REFERENCE TO SEQ ID NO: 32):

| CD4 epitope | Sequence |
|---|---|
| p1014-1031 | ENQKVKWEQELCSVRLTL |
| p1094-1111 | HENENYLLHENCMLKKEI |
| p1124-1141 | QYQEKENKYFEDIKILKE |
| p1134-1151 | EDIKILKEKNAELQMTLK |
| p1164-1181 | YSGQLKVLIAENTMLTSK |
| p1254-1271 | SEAQRKSKSLKINLNLYAG |
| p1264-1281 | KINLNYAGDALRENTLVS |
| p1344-1361 | ADNKSKITIDIHFLERKM |
| p1364-1381 | HLLKEKNEEIFNYNNHLK |
| p1374-1391 | FNYNNHLKNRIYQYEKEK |

TABLE 7

NY-BR-1 PEPTIDES RECOGNIZED BY CD8+ T CELLS:

| CD8 epitope | Sequence |
|---|---|
| p1214-1231 | TSRKSQEPAFHIAGDACL |
| p1224-1241 | HIAGDACLQRKMNVDVSS |
| p1264-1281 | KINLNYAGDALRENTLVS |
| p1274-1291 | LRENTLVSEHAQRDQRET |
| p1334-1351 | QQQLVHAHKKADNKSKIT |

All amino acid positions are by reference to SEQ ID NO: 32.

The foregoing examples describe the isolation of a nucleic acid molecule which encodes a cancer associated antigen. "Associated" is used herein because while it is clear that the relevant molecule was expressed by several types of cancer, other cancers, not screened herein, may also express the antigen.

The invention relates to nucleic acid molecules which encode the antigens encoded by, e.g., SEQ ID NOS: 1, 3, 8, 15, 22, 26 and 31 as well as the antigens encoded thereby, such as the proteins with the amino acid sequences of SEQ ID NOS: 5, 6, 7, 16, 23, 27, 30 and 32. It is to be understood that all sequences which encode the recited antigen are a part of the invention. Also a part of the invention are those nucleic acid molecules which have complementary nucleotide sequences which hybridize to the referred sequences, under stringent conditions. "Stringent conditions" as used herein refers, e.g., to prehybridization in 6×SSC/0.05 BLOTTO for 2 hours, followed by adding a probe mixed with salmon sperm DNA and overnight incubation at 68° C., followed by two one minute washes with 2×SSC/0.2% room temperature, and then three twenty minute washes with 2×SSC/0.2% SDS (68° C.). An optional additional one or two high stringency washes with 0.2×SSC/0.2% SDS, for 20 minutes, at 68° C., may be included.

Also a part of the invention are proteins, polypeptides, and peptides, which comprise, e.g., at least nine consecutive amino acids found in SEQ ID NO: 23 or 32, or at least nine consecutive amino acids of the amino acids of SEQ ID NO: 30 or 32. Proteins, polypeptides and peptides comprising nine or more amino acids of SEQ ID NO: 5, 6, 7, 16 or 27 are also a part of the invention. Especially preferred are peptides comprising or consisting of amino acids 102-111, 904-912, or 1262-1270 of SEQ ID NO: 23, which are paralleled in SEQ ID NO: 32. Such peptides may, but do not necessarily provoke CTL responses when complexed with an HLA molecule, such as an HLA-A2 molecule. They may also bind to different MHC or HLA molecules, including, but not being limited to, HLA-A1, A2, A3, B7, B8, Cw3, Cw6, or serve, e.g., as immunogens, as part of immunogenic cocktail compositions, where they are combined with other proteins or polypeptides, and so forth. Also a part of the invention are the nucleic acid molecules which encode these molecules, such as "minigenes," expression vectors that include the coding regions, recombinant cells containing these, and so forth. All are a part of the invention.

Also a part of the invention are expression vectors which incorporate the nucleic acid molecules of the invention, in operable linkage (i.e., "operably linked") to a promoter. Construction of such vectors, such as viral (e.g., adenovirus or Vaccinia virus) or attenuated viral vectors is well within the skill of the art, as is the transformation or transfection of cells, to produce eukaryotic cell lines, or prokaryotic cell strains which encode the molecule of interest. Exemplary of the host cells which can be employed in this fashion are COS cells, CHO cells, yeast cells, insect cells (e.g., *Spodoptera frugiperda*), NIH 3T3 cells, and so forth. Prokaryotic cells, such as *E. coli* and other bacteria may also be used. Any of these cells can also be transformed or transfected with further nucleic acid molecules, such as those encoding cytokines, e.g., interleukins such as IL-2, 4, 6, or 12 or HLA or MHC molecules.

Also a part of the invention are the antigens described herein, both in original form and in any different post translational modified forms. The molecules are large enough to be antigenic without any posttranslational modification, and hence are useful as immunogens, when combined with an adjuvant (or without it), in both precursor and post-translationally modified forms. Antibodies produced using these antigens, both poly and monoclonal, are also a part of the invention as well as hybridomas which make monoclonal antibodies to the antigens. The whole protein can be used therapeutically, or in portions, as discussed infra. Also a part of the invention are antibodies against this antigen, be these polyclonal, monoclonal, reactive fragments, such as Fab, $(F(ab)_2$, and other fragments, as well as chimeras, humanized antibodies, recombinantly produced antibodies, and so forth.

As is clear from the disclosure, one may use the proteins and nucleic acid molecules of the invention diagnostically. The SEREX methodology discussed herein is premised on an immune response to a pathology associated antigen. Hence, one may assay for the relevant pathology via, e.g., testing a body fluid sample of a subject, such as serum, for reactivity with the antigen per se. Reactivity would be deemed indicative of possible presence of the pathology. So, too, could one assay for the expression of any of the antigens via any of the standard nucleic acid hybridization assays which are well known to the art, and need not be elaborated upon herein. One could assay for antibodies against the subject molecules, using standard immunoassays as well.

As was shown in, e.g., examples 22 & 23, the invention relates in particular to methods for determining if cancer is present, such as breast cancer or pancreatic cancer, by assaying for expression of NY-BR-1, as defined supra, via a nucleotide based assay, such as polymerase chain reaction (PCR) or some other form of nucleotide hybridization assay, a protein based assay, such as an immunoassay, or a peptide based assay where one either looks for, or utilizes, CD8$^+$ cells which react specifically with complexes of peptides and their partner HLA molecule, such as LLSHGAVIEV (amino acids 102-111 of SEQ ID NO: 23) or SLSKILDTV (amino acids 904-912 of SEQ ID NO: 23), and HLA-A2. As with the nucleotide and protein based assays, these peptide based assays are especially useful in determining breast and/or pancreatic cancer. The assays of the invention, in all forms, can be used to determine presence, progression, and/or regression of cancer, such as breast and/or pancreatic cancer, and can then be used to determine the efficacy of therapeutic regimes, especially when the regime is directed against breast and/or pancreatic cancer.

Analysis of SEQ ID NO: 1, 3, 4, 8, 15, 22, 26 and 31 will show that there are 5' and 3' non-coding regions presented therein. The invention relates to those isolated nucleic acid molecules which contain at least the coding segment, and which may contain any or all of the non-coding 5' and 3' portions.

Also a part of the invention are portions of the relevant nucleic acid molecules which can be used, for example, as oligonucleotide primers and/or probes, such as one or more of SEQ ID NOS: 9, 10, 11, 12, 13, 14, 17, 18,20, 21, 24, 25, 28, and 29 as well as amplification products like nucleic acid molecules comprising at least nucleotides 305-748 of SEQ ID NO: 1, or amplification products described in the examples, including those in examples 12, 14, etc.

As was discussed supra, study of other members of the "CT" family reveals that these are also processed to peptides which provoke lysis by cytolytic T cells. There has been a great deal of work on motifs for various MHC or HLA molecules, which is applicable here. Hence, a further aspect of the invention is a therapeutic method, wherein one or more peptides derived from the antigens of the invention which bind to an HLA molecule on the surface of a patient's tumor cells are administered to the patient, in an amount sufficient for the peptides to bind to the MHC/HLA molecules, and provoke lysis by T cells. Any combination of peptides may be used. These peptides, which may be used alone or in combination, as well as the entire protein or immunoreactive portions thereof, may be administered to a subject in need thereof, using any of the standard types of administration, such as intravenous, intradermal, subcutaneous, oral, rectal, and transdermal administration. Standard pharmaceutical carriers, adjuvants, such as saponins, GM-CSF, and interleukins and so forth may also be used. Further, these peptides and proteins may be formulated into vaccines with the listed material, as may dendritic cells, or other cells which present relevant MHC/peptide complexes.

Of particular interest, are peptides shown to be natural epitopes of the NY-BR-1 molecule, such as LLSHGAVIEV (amino acids 102-111 of SEQ ID NO: 23) and SLSKILDTV (amino acids 904-912 of SEQ ID NO: 23). By "natural epitopes" is meant that CD8$^+$ cells taken from patients with cancer recognize and lyse cells which present these peptides on their surface. It is more desirable to use peptides which have been shown to be naturally occurring epitopes in an in vivo context, because these peptides can lead to expansion of pre-existing populations of relevant CD8$^+$ cells. In parallel, CD8$^+$ cells which are specific to the complexes can be used therapeutically. Hence, in any of the therapeutic approaches discussed herein relating to peptides or minigenes, it is especially preferred to use one or both of these peptide sequences, or minigenes which encode them.

Similarly, the invention contemplates therapies wherein nucleic acid molecules which encode the proteins of the invention, one or more or peptides which are derived from these proteins are incorporated into a vector, such as a Vaccinia or adenovirus based vector, to render it transfectable into eukaryotic cells, such as human cells. Nucleic acid molecules which encode one or more of the peptides may be incorporated into these vectors, which are then the major constituent of nucleic acid bases therapies.

Any of these assays can also be used in progression/regression studies. One can monitor the course of abnormality involving expression of these antigens simply by monitoring levels of the protein, its expression, antibodies against it and so forth using any or all of the methods set forth supra.

It should be clear that these methodologies may also be used to track the efficacy of a therapeutic regime. Essentially, one can take a baseline value for a protein of interest using any of the assays discussed supra, administer a given therapeutic agent, and then monitor levels of the protein thereafter, observing changes in antigen levels as indicia of the efficacy of the regime.

As was indicated supra, the invention involves, inter alia, the recognition of an "integrated" immune response to the molecules of the invention. One ramification of this is the ability to monitor the course of cancer therapy. In this method, which is a part of the invention, a subject in need of the therapy receives a vaccination of a type described herein. Such a vaccination results, e.g., in a T cell response against cells presenting HLA/peptide complexes on their cells. The response also includes an antibody response, possibly a result of the release of antibody provoking proteins via the lysis of cells by the T cells. Hence, one can monitor the effect of a vaccine, by monitoring an antibody response. As is indicated, supra, an increase in antibody titer may be taken as an indicia of progress with a vaccine, and vice versa. Hence, a further aspect of the invention is a method for monitoring efficacy of a vaccine, following administration thereof, by determining levels of antibodies in the subject which are specific for the vaccine itself, or a large molecule of which the vaccine is a part.

The identification of the subject proteins as being implicated in pathological conditions such as cancer also suggests a number of therapeutic approaches in addition to those discussed supra. The experiments set forth supra establish that antibodies are produced in response to expression of the protein. Hence, a further embodiment of the invention is the treatment of conditions which are characterized by aberrant or abnormal levels of one or more of the proteins, via administration of antibodies, such as humanized antibodies, antibody fragments, and so forth. These may be tagged or labelled with appropriate cystostatic or cytotoxic reagents.

T cells may also be administered. It is to be noted that the T cells may be elicited in vitro using immune responsive cells such as dendritic cells, lymphocytes, or any other immune responsive cells, and then reperfused into the subject being treated.

Note that the generation of T cells and/or antibodies can also be accomplished by administering cells, preferably treated to be rendered non-proliferative, which present relevant T cell or B cell epitopes for response, such as the epitopes discussed supra.

The therapeutic approaches may also include antisense therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the known BCG vaccine, and so forth.

Also a part of this invention are antibodies, e.g., polyclonal and monoclonal, and antibody fragments e.g., single chain Fv, Fab, diabodies etc., that specifically bind the peptides or HLA/peptide complexes disclosed herein. Preferably the antibodies, the antibody fragments and T cell receptors bind the HLA/peptide complexes in a peptide-specific manner. Such antibodies are useful, for example, in identifying cells presenting the HLA/peptide complexes, particularly complexes comprising an HLA-A1, A2, A3, A26, HLA-B7, B8, B15, B27, B35, B44, B51, B57, Cw3, or Cw6 molecule, preferably HLA-A2 or B57, and a peptide consisting essentially of the sequences described supra, such as amino acids 102-111, 904-912, or 1262-1270 of SEQ ID NO: 23.

Such antibodies are also useful in promoting the regression or inhibiting the progression of a tumor which expresses complexes of the HLA and peptide. Polyclonal antisera and monoclonal antibodies specific to the peptides or HLA/peptide complexes of this invention may be generated according to standard procedures. See e.g., Catty, D., *Antibodies, A Practical Approach*, Vol. 1, IRL Press, Washington D.C. (1988); Klein, *J. Immunology: The Science of Cell-Non-Cell Discrimination*, John Wiley and Sons, New York (1982); Kennett, R., et al., *Monoclonal Antibodies, Hybridoma, A New Dimension In Biological Analyses*, Plenum Press, New York (1980); Campbell, A., *Monoclonal Antibody Technology, in Laboratory Techniques and Biochemistry and Molecular Biology*, Vol. 13 (Burdon, R., et al. EDS.), Elsevier Amsterdam (1984); Eisen, H. N., *Microbiology*, third edition, Davis, B. D., et al. EDS. (Harper & Rowe, Philadelphia (1980); Kohler and Milstein, *Nature*, 256:495 (1975) all incorporated herein by reference.) Methods for identifying Fab molecules endowed with the antigen-specific, HLA-restricted specificity of T cells has been described by Denkberg, et al., *Proc. Natl. Acad. Sci.*, 99:9421-9426 (2002) and Cohen, et al., *Cancer Research*, 62:5835-5844 (2002) (both incorporated herein by reference). Methods for generating and identifying other antibody molecules, e.g., scFv and diabodies are well known in the art, see e.g., Bird, et al., *Science*, 242:423-426 (1988); Huston, et al., *Proc. Natl. Acad. Sci.*, 85:5879-5883 (1988); Mallender and Voss, *J. Biol. Chem.*, 269:199-206 (1994); Ito and Kurosawa, *J. Biol. Chem.*, 27:20668-20675 (1993), and; Gandecha, et al., *Prot. Express Purif*, 5:385-390 (1994)(all incorporated herein by reference).

The antibodies of this invention can be used for experimental purposes (e.g. localization of the HLA/peptide complexes, immunoprecipitations, Western blots, flow cytometry, ELISA etc.) as well as diagnostic or therapeutic purposes, e.g., assaying extracts of tissue biopsies for the presence of HLA/peptide complexes, targeting delivery of cytotoxic or cytostatic substances to cells expressing the appropriate HLA/peptide complex. The antibodies of this invention are useful for the study and analysis of antigen presentation on tumor cells and can be used to assay for changes in the HLA/peptide complex expression before, during or after a treatment protocol, e.g., vaccination with peptides, antigen presenting cells, HLA/peptide tetramers, adoptive transfer or chemotherapy. The antibodies and antibody fragments of this invention may be coupled to diagnostic labeling agents for imaging of cells and tissues that express the HLA/peptide complexes or may be coupled to therapeutically useful agents by using standard methods well-known in the art. The antibodies also may be coupled to labeling agents for imaging e.g., radiolabels or fluorescent labels, or may be coupled to, e.g., biotin or antitumor agents, e.g., radioiodinated compounds, toxins such as ricin, methotrexate, cytostatic or cytolytic drugs, etc. Examples of diagnostic agents suitable for conjugating to the antibodies of this invention include e.g., barium sulfate, diatrizoate sodium, diatrizoate meglumine, iocetamic acid, iopanoic acid, ipodate calcium, metrizamide, tyropanoate sodium and radiodiagnostics including positron emitters such as fluorine-18 and carbon-11, gamma emitters such as iodine-123, technitium-99m, iodine-131 and indium-111, nuclides for nuclear magnetic resonance such as fluorine and gadolinium. As used herein, "therapeutically useful agents" include any therapeutic molecule which are preferably targeted selectively to a cell expressing the HLA/peptide complexes, including antineoplastic agents, radioiodinated compounds, toxins, other cytostatic or cytolytic drugs. Antineoplastic therapeutics are well known and include: aminoglutethimide, azathioprine, bleomycin sulfate, busulfan, carmustine, chlorambucil, cisplatin, cyclophosphamide, cyclosporine, cytarabidine, dacarbazine, dactinomycin, daunorubicin, doxorubicin, taxol, etoposide, fluorouracil, interferon-.alpha., lomustine, mercaptopurine, methotrexate, mitotane, procarbazine HCl, thioguanine, vinblastine sulfate and vincristine sulfate. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division). Toxins can be proteins such as, for example, pokeweed anti-viral protein, cholera toxin, pertussis toxin, ricin, gelonin, abrin, diphtheria exotoxin, or *Pseudomonas* exotoxin. Toxin moieties can also be high energy-emitting radionuclides such as $^{131}$I, $^{90}$Y or any other alpha, beta and auger emitting that are known within the art. The antibodies may be administered to a subject having a pathological condition characterized by the presentation of the HLA/peptide complexes of this invention, e.g., melanoma or other cancers, in an amount sufficient to alleviate the symptoms associated with the pathological condition.

Soluble T cell receptors (TcR) which specifically bind to the HLA/peptide complexes described herein are also an aspect of this invention. In their soluble form T cell receptors are analogous to a monoclonal antibody in that they bind to HLA/peptide complex in a peptide-specific manner. Immobilized TcRs or antibodies may be used to identify and purify unknown peptide/HLA complexes which may be involved in cellular abnormalities. Methods for identifying and isolating soluble TcRs are known in the art, see for example WO 99/60119, WO 99/60120 (both incorporated herein by reference) which describe synthetic multivalent T cell receptor complex for binding to peptide-MHC complexes. Recombinant, refolded soluble T cell receptors are specifically described. Such receptors may be used for delivering therapeutic agents or detecting specific peptide-MHC complexes expressed by tumor cells. WO 02/088740 (incorporated by reference) describes a method for identifying a substance that binds to a peptide-MHC complex. A peptide-MHC complex is formed between a predetermined MHC and peptide known to bind to such predetermined MHC. The complex is then use to screen or select an entity that binds to the peptide-MHC complex such as a T cell receptor. The method could also be applied to the selection of monoclonal antibodies that bind to the predetermined peptide-MHC complex.

Also a part of this invention are nucleic acid molecules encoding the antibodies and T cell receptors of this invention and host cells, e.g., human T cells, transformed with a nucleic acid molecule encoding a recombinant antibody or antibody fragment, e.g., scFv or Fab, or a TcR specific for a predesignated HLA/peptide complex as described herein, particularly a complex wherein the HLA molecule is an HLA-A1, A2, A3, A26, HLA-B7, B8, B15, B27, B35, B44, B51, B57, Cw3 or Cw6 molecule, preferably HLA-A2 or B57, and the peptide is encoded by nucleotide sequence corresponding to a nucleotide sequence found in SEQ ID NO: 31.

Recombinant Fab or TcR specific for a predesignated HLA/peptide complex in T cells have been described in, e.g., Willemsen, et al., "A phage display selected Fab fragment with MHC class I-restricted specificity for MAGE-A1 allows for retargeting of primary human T lymphocytes" *Gene Ther.*, 2001 November; 8(21):1601-8. and Willemsen, et al., "Grafting primary human T lymphocytes with cancer-specific chimeric single chain and two chain TCR". *Gene Ther.*, 2000 August; 7(16):1369-77. (both incorporated herein by reference) and have applications in an autologous T cell transfer setting. The autologous T cells, transduced to express recombinant antibody or TcR, may be infused into a patient having an pathological condition associated with cells expressing the HLA/peptide complex. The transduced T cells are administered in an amount sufficient to inhibit the progression or alleviate at least some of the symptoms associated with the pathological condition.

This invention also relates to a method for promoting regression or inhibiting progression of a tumor in a subject in need thereof wherein the tumor expresses a complex of HLA and peptide. The method comprises administering an antibody, antibody fragment or soluble T cell receptor, which specifically binds to the HLA/peptide complex, or by administering cells transduced so that they express those antibodies or TcR in amounts that are sufficient to promote the regression or inhibit progression of the tumor expressing the HLA/peptide complex, e.g., a melanoma or other cancer. Preferably the HLA is an HLA-A2, or B57 and the peptide is an NY-BR-1 derived peptide preferably a peptide consisting of the sequences set forth supra, such as amino acids 102-111, 904-912, or 1262-1270 of SEQ ID NO: 23.

The antibodies, antibody fragments and soluble T cell receptors may be conjugated with, or administered in conjunction with, an antineoplastic agent, e.g., radioiodinated compounds, toxins such as ricin, methotrexate, or a cytostatic or cytolytic agent as discussed supra. See e.g., Pastan, et al., *Biochem. Biophys. Acta.*, 133:C1-C6 (1997), Lode, et al., *Immunol. Res.*, 21:279-288 (2000) and Wihoff, et al., *Curr. Opin. Mo. Ther.*, 3:53-62 (2001) (all incorporated herein by reference) for a discussion of the construction of recombinant immunotoxins, antibody fusions with cytokine molecules and bispecific antibody therapy or immunogene therapy.

Other features and applications of the invention will be clear to the skilled artisan, and need not be set forth herein. The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. An immunogenic composition comprising at least one peptide consisting of an amino acid sequence of from 8 to 18 consecutive amino acids in an amino acid sequences set forth in amino acids 1124-1141 of SEQ ID NO: 32, amino acids 1274-1291 of SEQ ID NO: 32, and amino acids 1374-1391 of SEQ ID NO: 32, and an adjuvant.

2. The immunogenic composition of claim 1, wherein said adjuvant is a saponin, a cytokine, or a GM-CSF.

3. The immunogenic composition comprising a plurality of peptides of claim 1.

4. An immunogenic composition comprising at least one peptide, the amino acid sequence of which consists of: amino acids 1014-1031 of SEQ ID NO: 32, amino acids 1094-1111 of SEQ ID NO: 32, amino acids 1124-1141 of SEQ ID NO: 32, amino acids 1134-1151 of SEQ ID NO: 32, amino acids 1164-1181 of SEQ ID NO: 32, amino acids 1214-1231 of SEQ ID NO: 32, amino acids 1224-1241 of SEQ ID NO: 32, amino acids 1254-1271 of SEQ ID NO: 32, amino acids 1264-1281 of SEQ ID NO: 32, amino acids 1274-1291 of SEQ ID NO: 32, amino acids 1334-1351 of SEQ ID NO: 32, amino acids 1344-1361 of SEQ ID NO: 32, amino acids 1374-1391 of SEQ ID NO: 32.

5. An isolated peptide consisting of an amino acid sequence of from 8 to 18 amino acids in an amino acid sequence set forth in amino acids 1124-1141 SEQ ID NO: 32, amino acids 1274-1291 of SEQ ID NO: 32, amino acids 1374-1391 of SEQ ID NO: 32.

6. An isolated peptide consisting of: amino acids 1014-1031 of SEQ ID NO: 32, amino acids 1094-1111 of SEQ ID NO: 32, amino acids 1124-1141 of SEQ ID NO: 32, amino acids 1134-1151 of SEQ ID NO: 32, amino acids 1164-1181 of SEQ ID NO: 32, amino acids 1214-1231 of SEQ ID NO: 32, amino acids 1224-1241 of SEQ ID NO: 32, amino acids 1254-1271 of SEQ ID NO: 32, amino acids 1264-1281 of SEQ ID NO: 32, amino acids 1274-1291 of SEQ ID NO: 32, amino acids 1334-1351 of SEQ ID NO: 32, amino acids 1344-1361 of SEQ ID NO: 32, amino acids 1364-1381 of SEQ ID NO: 32, or amino acids 1374-1391 of SEQ ID NO: 32.

7. The isolated peptide of claim 6, consisting of amino acids 1014-1031 of SEQ ID NO: 32.

8. The isolated peptide of claim 6, consisting of amino acids 1094-1111 of SEQ ID NO: 32.

9. The isolated peptide of claim 6, consisting of amino acids 1124-1141 of SEQ ID NO: 32.

10. The isolated peptide of claim 6, consisting of amino acids 1134-1151 of SEQ ID NO: 32.

11. The isolated peptide of claim 6, consisting of amino acids 1164-1181 of SEQ ID NO: 32.

12. The isolated peptide of claim 6, consisting of amino acids 1214-1231 of SEQ ID NO: 32.

13. The isolated peptide of claim 6, consisting of amino acids 1224-1241 of SEQ ID NO: 32.

14. The isolated peptide of claim 6, consisting of amino acids 1254-1271 of SEQ ID NO: 32.

15. The isolated peptide of claim 6, consisting of amino acids 1264-1281 of SEQ ID NO: 32.

16. The isolated peptide of claim 6, consisting of amino acids 1274-1291 of SEQ ID NO: 32.

17. The isolated peptide of claim 6, consisting of amino acids 1334-1351 of SEQ ID NO: 32.

18. The isolated peptide of claim 6, consisting of amino acids 1344-1361 of SEQ ID NO: 32.

19. The isolated peptide of claim 6, consisting of amino acids 1364-1381 of SEQ ID NO: 32.

20. The isolated peptide of claim 6, consisting of amino acids 1374-1391 of SEQ ID NO: 32.

21. The isolated peptide of claim 5, consisting of amino acids 1124-1141 of SEQ ID NO: 32.

22. The isolated peptide of claim 5, consisting of amino acids 1274-1291 of SEQ ID NO: 32.

23. The isolated peptide of claim 5, consisting of amino acids 1374-1391 of SEQ ID NO: 32.

* * * * *